(12) United States Patent
Gillevet

(10) Patent No.: US 11,091,813 B2
(45) Date of Patent: Aug. 17, 2021

(54) MULTITAG SEQUENCING ECOGENOMICS ANALYSIS

(71) Applicant: BIOSPHEREX, LLC, Potomac Falls, VA (US)

(72) Inventor: Patrick M. Gillevet, Oakton, VA (US)

(73) Assignee: PRESCIENT METABIOMICS JV, LLC, Chicago, IL (US)

( * ) Notice: Subject to any disclaimer, the term of this patent is extended or adjusted under 35 U.S.C. 154(b) by 302 days.

(21) Appl. No.: 15/240,525

(22) Filed: Aug. 18, 2016

(65) Prior Publication Data

US 2016/0355874 A1    Dec. 8, 2016

Related U.S. Application Data

(63) Continuation of application No. 14/066,967, filed on Oct. 30, 2013, now Pat. No. 9,453,262, which is a continuation of application No. 12/515,262, filed as application No. PCT/US2007/084840 on Nov. 15, 2007, now Pat. No. 8,603,749.

(60) Provisional application No. 60/858,948, filed on Nov. 15, 2006.

(51) Int. Cl.
*C12Q 1/689* (2018.01)
*C12Q 1/6858* (2018.01)

(52) U.S. Cl.
CPC .......... *C12Q 1/689* (2013.01); *C12Q 1/6858* (2013.01); *C12Q 2600/156* (2013.01); *C12Q 2600/16* (2013.01)

(58) Field of Classification Search
None
See application file for complete search history.

*Primary Examiner* — Joseph Woitach
(74) *Attorney, Agent, or Firm* — Morgan, Lewis & Bockius LLP

(57) ABSTRACT

Embodiments of the invention herein described relate to multiplex polynucleotide sequence analysis without the use of size separation methods or blotting. In certain particulars the invention relates to multiplex sequencing using massively parallel sequencing methods, such as pyrosequencing methods and sequencing by synthesis. The invention provides increased throughput, increased accuracy of enumerating sample components, and the ability to analyze greater numbers of samples simultaneously or serially on presently available systems, as well as others yet to be developed. In certain of its embodiments the invention relates to the analysis of complex microbial communities, particularly to in-depth analysis thereof in large numbers of samples.

29 Claims, 13 Drawing Sheets

Specification includes a Sequence Listing.

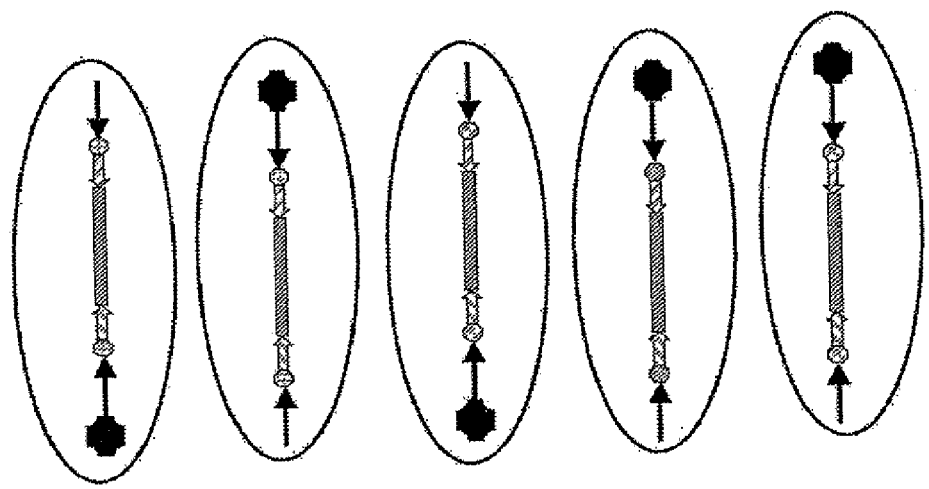
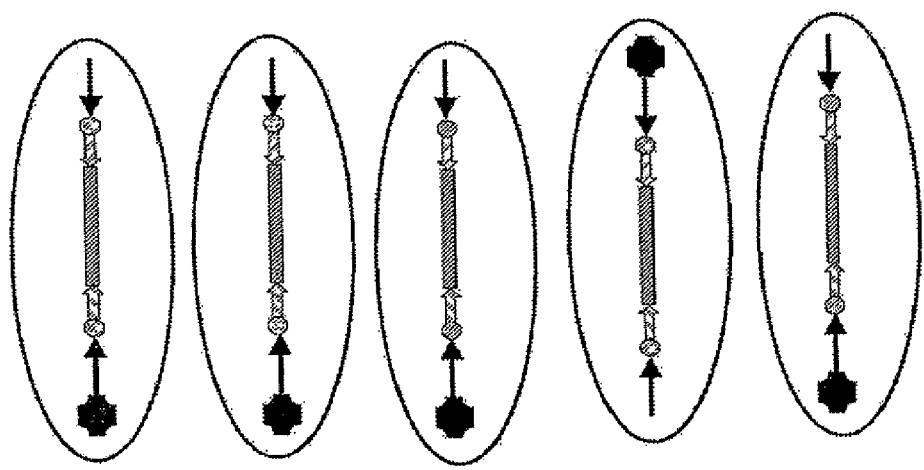
Figure 2 B

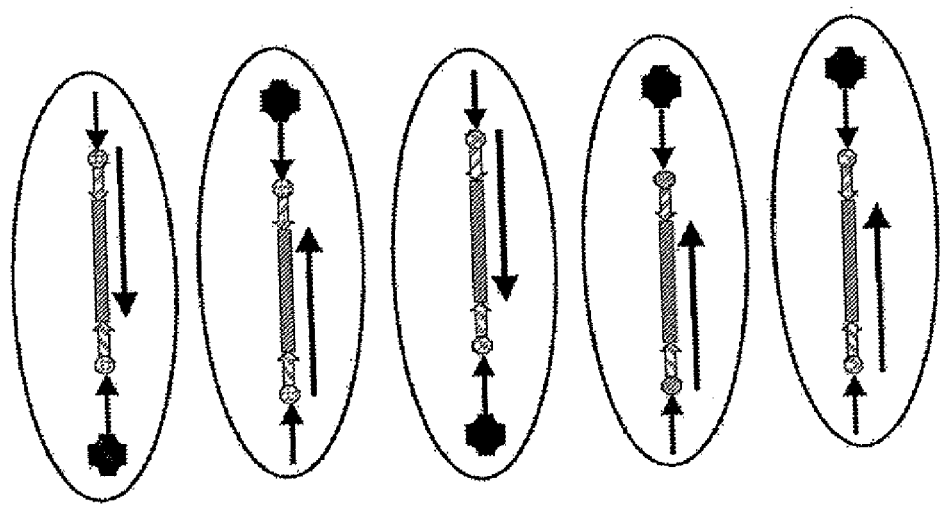
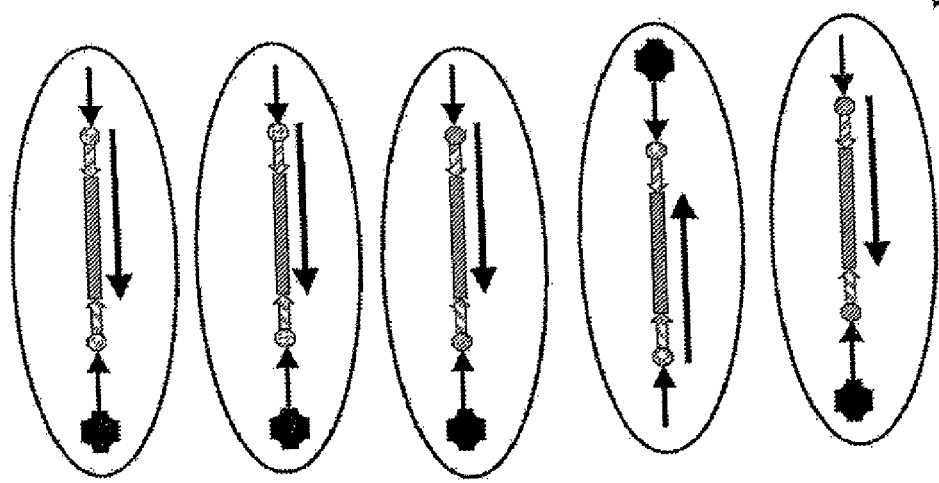
Figure 2C

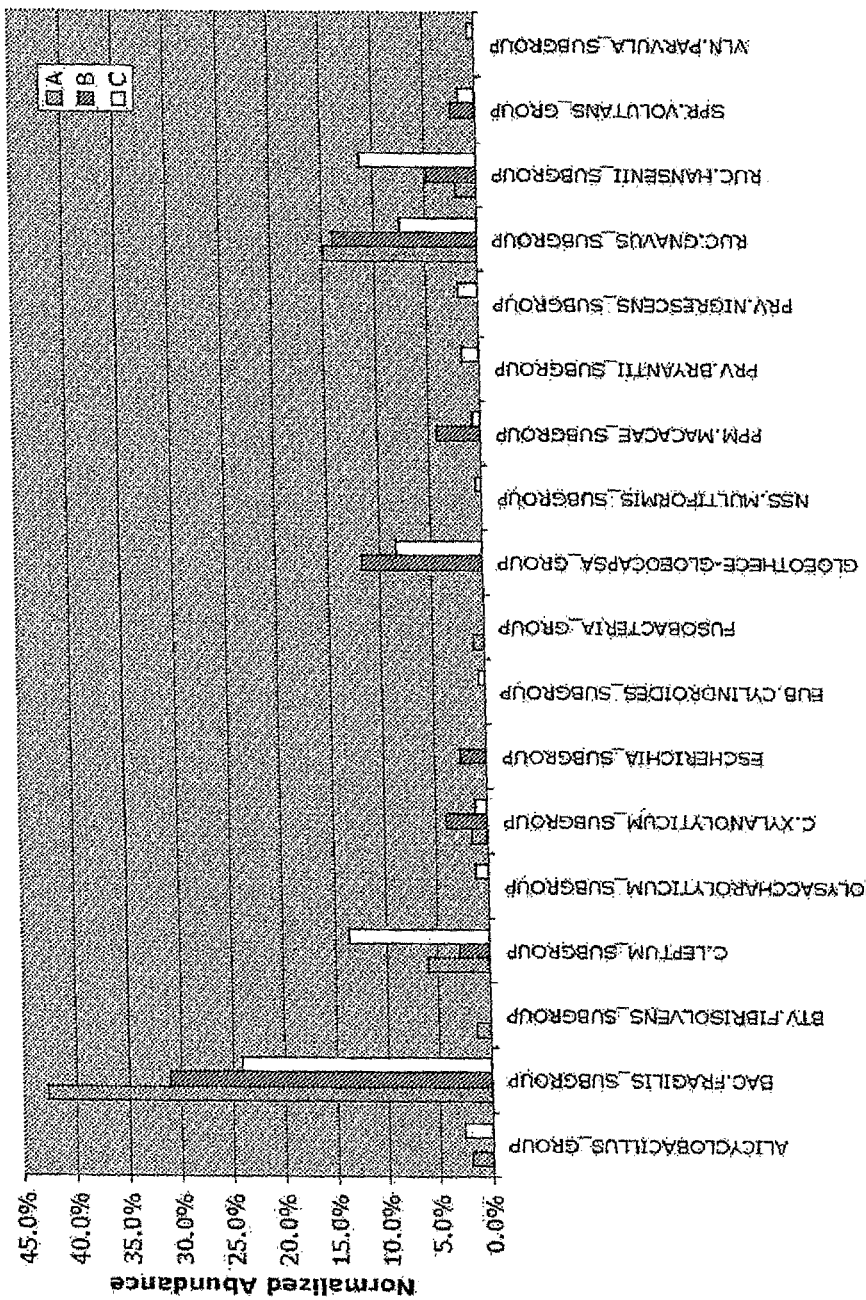

| FAMILY | Forward Primer | Reverse Primer | RATIO | Forward Primer | Reverse Primer | RATIO |
|---|---|---|---|---|---|---|
| | ALD309FO | ALD309RO | Forward/Reverse | ALD309FP | ALD309RP | Forward/Reverse |
| Acidaminococcaceae | 0.8% | 0.9% | 88.5% | 0.2% | 0.5% | 31.7% |
| Actinomycetales | 2.4% | 2.0% | 120.7% | 1.7% | 1.7% | 97.6% |
| Bacteroidaceae | 58.4% | 62.8% | 93.1% | 48.7% | 50.5% | 96.6% |
| Brucellaceae | | | | 7.5% | 3.1% | 239.1% |
| Burkholderiaceae | | | | 0.4% | 0.2% | 184.9% |
| Clostridiaceae | 14.5% | 9.6% | 150.7% | 14.9% | 9.7% | 153.7% |
| Comamonadaceae | 0.3% | | | 0.2% | 0.3% | 55.5% |
| Coriobacteriales | 0.8% | 0.9% | 94.8% | 0.5% | 0.6% | 73.9% |
| Enterobacteriaceae | 0.2% | | | 3.6% | 2.9% | 124.1% |
| Eubacteriaceae | 1.8% | 1.6% | 115.9% | 2.1% | 1.8% | 115.2% |
| Flavobacteriaceae | 0.5% | | | 1.3% | 2.1% | 62.9% |
| Incertae sedis 9 | 3.3% | 4.2% | 78.6% | 3.1% | 2.9% | 105.6% |
| Lachnospiraceae | 5.7% | 8.7% | 65.6% | 3.2% | 7.7% | 42.0% |
| Lactobacillaceae | | 0.3% | | 1.3% | 0.5% | 269.4% |
| Peptococcaceae | | | | 0.2% | 0.3% | 83.2% |
| Peptostreptococcaceae | 3.3% | 3.3% | 102.1% | 3.5% | 2.8% | 124.4% |
| Phyllobacteriaceae | | | | 1.6% | 6.2% | 26.2% |
| Porphyromonadaceae | 2.1% | 2.0% | 109.0% | 2.2% | 2.0% | 107.1% |
| Prevotellaceae | 3.0% | 2.0% | 155.7% | 1.2% | 2.2% | 52.0% |
| Rikenellaceae | 1.1% | 0.9% | 129.3% | 0.5% | 0.8% | 64.7% |
| Streptococcaceae | 0.5% | 0.3% | 181.1% | 0.6% | 0.4% | 147.9% |

Figure 5

| 1 | 25 | 49 | 73 | 97 | 121 | 145 | 169 | 193 |
|---|---|---|---|---|---|---|---|---|
| AGACAG | AGTGAG | ATGCAG | CATACA | CGCTAG | GCGCAG | GTCACA | TACTAG | TCAGAG |
| AGACGT | AGTGCA | ATGCGT | CATAGT | CGCTCA | GCGCGT | GTCAGT | TACTCA | TCAGCA |
| AGACTC | AGTGTC | ATGCTC | CATATC | CGCTGT | GCGCTC | GTCATC | TACTGT | TCAGTC |
| AGAGAG | ATACAG | ATGTAG | CATCAG | CGTACA | GCGTAG | GTCGAG | TAGACA | TCATAG |
| AGAGCA | ATACGT | ATGTCA | CATCGT | CGTAGT | GCGTCA | GTCGCA | TAGAGT | TCATCA |
| AGAGTC | ATACTC | ATGTGT | CATCTC | CGTATC | GCGTGT | GTCGTC | TAGATC | TCATGT |
| AGATAG | ATAGAG | CACACA | CATGAG | CGTCAG | GCTACA | GTCTAG | TAGCAG | TCGACA |
| AGATCA | ATAGCA | CACAGT | CATGCA | CGTCGT | GCTAGT | GTCTCA | TAGCGT | TCGAGT |
| AGATGT | ATAGTC | CACATC | CATGTC | CGTCTC | GCTATC | GTCTGT | TAGCTC | TCGATC |
| AGCACA | ATATAG | CACGAG | CGACAG | CGTGAG | GCTCAG | GTGACA | TAGTAG | TCGCAG |
| AGCAGT | ATATCA | CACGCA | CGACGT | CGTGCA | GCTCGT | GTGAGT | TAGTCA | TCGCGT |
| AGCATC | ATATGT | CACGTC | CGACTC | CGTGTC | GCTCTC | GTGATC | TAGTGT | TCGCTC |
| AGCGAG | ATCACA | CACTAG | CGAGAG | GCACAG | GCTGAG | GTGCAG | TATACA | TCGTAG |
| AGCGCA | ATCAGT | CACTCA | CGAGCA | GCACGT | GCTGCA | GTGCGT | TATAGT | TCGTCA |
| AGCGTC | ATCATC | CACTGT | CGAGTC | GCACTC | GCTGTC | GTGCTC | TATATC | TCGTGT |
| AGCTAG | ATCGAG | CAGACA | CGATAG | GCAGAG | GTACAG | GTGTAG | TATCAG | TCTACA |
| AGCTCA | ATCGCA | CAGAGT | CGATCA | GCAGCA | GTACGT | GTGTCA | TATCGT | TCTAGT |
| AGCTGT | ATCGTC | CAGATC | CGATGT | GCAGTC | GTACTC | GTGTGT | TATCTC | TCTATC |
| AGTACA | ATCTAG | CAGCAG | CGCACA | GCATAG | GTAGAG | GTGTCT | TATGAG | TCTCAG |
| AGTAGT | ATCTCA | CAGCGT | CGCAGT | GCATCA | GTAGCA | TACACA | TATGCA | TCTCGT |
| AGTATC | ATCTGT | CAGCTC | CGCATC | GCATGT | GTAGTC | TACAGT | TATGTC | TCTCTC |
| AGTCAG | ATGACA | CAGTAG | CGCGAG | GCGACA | GTATAG | TACATC | TCACAG | TCTGAG |
| AGTCGT | ATGAGT | CAGTCA | CGCGCA | GCGAGT | GTATCA | TACGAG | TCACGT | TCTGCA |
| AGTCTC | ATGATC | CAGTGT | CGCGTC | GCGATC | GTATGT | TACGTC | TCACTC | TCTGTC |
| 24 | 48 | 72 | 96 | 120 | 144 | 168 | 192 | 216 |

FORWARD TAGGED ADAPTER PRIMER

| Primer Pair | ADAPTER A | TAG | Forward 16S rRNA Primer |
|---|---|---|---|
| 1 | GCCTCCCTCGCGCCATCAG | AGACGT | AGAGTTTGATCMTGGCTCAG |
| 2 | GCCTCCCTCGCGCCATCAG | AGACTC | AGAGTTTGATCMTGGCTCAG |
| 3 | GCCTCCCTCGCGCCATCAG | AGAGTC | AGAGTTTGATCMTGGCTCAG |
| 4 | GCCTCCCTCGCGCCATCAG | AGATGT | AGAGTTTGATCMTGGCTCAG |
| 5 | GCCTCCCTCGCGCCATCAG | AGCAGT | AGAGTTTGATCMTGGCTCAG |
| 6 | GCCTCCCTCGCGCCATCAG | AGCATC | AGAGTTTGATCMTGGCTCAG |
| 7 | GCCTCCCTCGCGCCATCAG | AGCGTC | AGAGTTTGATCMTGGCTCAG |
| 8 | GCCTCCCTCGCGCCATCAG | AGCTGT | AGAGTTTGATCMTGGCTCAG |
| 9 | GCCTCCCTCGCGCCATCAG | AGTAGT | AGAGTTTGATCMTGGCTCAG |
| 10 | GCCTCCCTCGCGCCATCAG | AGTATC | AGAGTTTGATCMTGGCTCAG |
| 11 | GCCTCCCTCGCGCCATCAG | AGTCGT | AGAGTTTGATCMTGGCTCAG |
| 12 | GCCTCCCTCGCGCCATCAG | AGTCTC | AGAGTTTGATCMTGGCTCAG |
| 13 | GCCTCCCTCGCGCCATCAG | AGTGTC | AGAGTTTGATCMTGGCTCAG |
| 14 | GCCTCCCTCGCGCCATCAG | ATACGT | AGAGTTTGATCMTGGCTCAG |
| 15 | GCCTCCCTCGCGCCATCAG | ATACTC | AGAGTTTGATCMTGGCTCAG |
| 16 | GCCTCCCTCGCGCCATCAG | ATAGTC | AGAGTTTGATCMTGGCTCAG |
| 17 | GCCTCCCTCGCGCCATCAG | ATATGT | AGAGTTTGATCMTGGCTCAG |
| 18 | GCCTCCCTCGCGCCATCAG | ATCAGT | AGAGTTTGATCMTGGCTCAG |
| 19 | GCCTCCCTCGCGCCATCAG | ATCATC | AGAGTTTGATCMTGGCTCAG |
| 20 | GCCTCCCTCGCGCCATCAG | ATCGTC | AGAGTTTGATCMTGGCTCAG |
| 21 | GCCTCCCTCGCGCCATCAG | ATCTGT | AGAGTTTGATCMTGGCTCAG |
| 22 | GCCTCCCTCGCGCCATCAG | ATGAGT | AGAGTTTGATCMTGGCTCAG |
| 23 | GCCTCCCTCGCGCCATCAG | ATGATC | AGAGTTTGATCMTGGCTCAG |
| 24 | GCCTCCCTCGCGCCATCAG | ATGCGT | AGAGTTTGATCMTGGCTCAG |
| 25 | GCCTCCCTCGCGCCATCAG | ATGCTC | AGAGTTTGATCMTGGCTCAG |
| 26 | GCCTCCCTCGCGCCATCAG | ATGTGT | AGAGTTTGATCMTGGCTCAG |
| 27 | GCCTCCCTCGCGCCATCAG | CACAGT | AGAGTTTGATCMTGGCTCAG |
| 28 | GCCTCCCTCGCGCCATCAG | CACATC | AGAGTTTGATCMTGGCTCAG |
| 29 | GCCTCCCTCGCGCCATCAG | CACGTC | AGAGTTTGATCMTGGCTCAG |
| 30 | GCCTCCCTCGCGCCATCAG | CACTGT | AGAGTTTGATCMTGGCTCAG |
| 31 | GCCTCCCTCGCGCCATCAG | CAGAGT | AGAGTTTGATCMTGGCTCAG |
| 32 | GCCTCCCTCGCGCCATCAG | CAGATC | AGAGTTTGATCMTGGCTCAG |
| 33 | GCCTCCCTCGCGCCATCAG | CAGCGT | AGAGTTTGATCMTGGCTCAG |
| 34 | GCCTCCCTCGCGCCATCAG | CAGCTC | AGAGTTTGATCMTGGCTCAG |
| 35 | GCCTCCCTCGCGCCATCAG | CAGTGT | AGAGTTTGATCMTGGCTCAG |
| 36 | GCCTCCCTCGCGCCATCAG | CATAGT | AGAGTTTGATCMTGGCTCAG |
| 37 | GCCTCCCTCGCGCCATCAG | CATATC | AGAGTTTGATCMTGGCTCAG |
| 38 | GCCTCCCTCGCGCCATCAG | CATCGT | AGAGTTTGATCMTGGCTCAG |
| 39 | GCCTCCCTCGCGCCATCAG | CATCTC | AGAGTTTGATCMTGGCTCAG |
| 40 | GCCTCCCTCGCGCCATCAG | CATGTC | AGAGTTTGATCMTGGCTCAG |
| 41 | GCCTCCCTCGCGCCATCAG | CGACGT | AGAGTTTGATCMTGGCTCAG |
| 42 | GCCTCCCTCGCGCCATCAG | CGACTC | AGAGTTTGATCMTGGCTCAG |
| 43 | GCCTCCCTCGCGCCATCAG | CGAGTC | AGAGTTTGATCMTGGCTCAG |
| 44 | GCCTCCCTCGCGCCATCAG | CGATGT | AGAGTTTGATCMTGGCTCAG |
| 45 | GCCTCCCTCGCGCCATCAG | CGCAGT | AGAGTTTGATCMTGGCTCAG |
| 46 | GCCTCCCTCGCGCCATCAG | CGCATC | AGAGTTTGATCMTGGCTCAG |
| 47 | GCCTCCCTCGCGCCATCAG | CGCGTC | AGAGTTTGATCMTGGCTCAG |
| 48 | GCCTCCCTCGCGCCATCAG | CGCTGT | AGAGTTTGATCMTGGCTCAG |
| 49 | GCCTCCCTCGCGCCATCAG | CGTAGT | AGAGTTTGATCMTGGCTCAG |
| 50 | GCCTCCCTCGCGCCATCAG | CGTATC | AGAGTTTGATCMTGGCTCAG |

FIGURE 7B

FORWARD TAGGED ADAPTER PRIMER

| Primer Pair | ADAPTER A | TAG | Forward 16S rRNA Primer |
|---|---|---|---|
| 51 | GCCTCCCTCGCGCCATCAG | CGTGGT | AGAGTTTGATCMTGGCTCAG |
| 52 | GCCTCCCTCGCGCCATCAG | CGTCTC | AGAGTTTGATCMTGGCTCAG |
| 53 | GCCTCCCTCGCGCCATCAG | CGTGCA | AGAGTTTGATCMTGGCTCAG |
| 54 | GCCTCCCTCGCGCCATCAG | CGTGTC | AGAGTTTGATCMTGGCTCAG |
| 55 | GCCTCCCTCGCGCCATCAG | TACAGT | AGAGTTTGATCMTGGCTCAG |
| 56 | GCCTCCCTCGCGCCATCAG | TACATC | AGAGTTTGATCMTGGCTCAG |
| 57 | GCCTCCCTCGCGCCATCAG | TACGTC | AGAGTTTGATCMTGGCTCAG |
| 58 | GCCTCCCTCGCGCCATCAG | TACTGT | AGAGTTTGATCMTGGCTCAG |
| 59 | GCCTCCCTCGCGCCATCAG | TAGAGT | AGAGTTTGATCMTGGCTCAG |
| 60 | GCCTCCCTCGCGCCATCAG | TAGATC | AGAGTTTGATCMTGGCTCAG |
| 61 | GCCTCCCTCGCGCCATCAG | TAGCGT | AGAGTTTGATCMTGGCTCAG |
| 62 | GCCTCCCTCGCGCCATCAG | TAGCTC | AGAGTTTGATCMTGGCTCAG |
| 63 | GCCTCCCTCGCGCCATCAG | TAGTGT | AGAGTTTGATCMTGGCTCAG |
| 64 | GCCTCCCTCGCGCCATCAG | TATAGT | AGAGTTTGATCMTGGCTCAG |
| 65 | GCCTCCCTCGCGCCATCAG | TATATC | AGAGTTTGATCMTGGCTCAG |
| 66 | GCCTCCCTCGCGCCATCAG | TATCGT | AGAGTTTGATCMTGGCTCAG |
| 67 | GCCTCCCTCGCGCCATCAG | TATCTC | AGAGTTTGATCMTGGCTCAG |
| 68 | GCCTCCCTCGCGCCATCAG | TATGTC | AGAGTTTGATCMTGGCTCAG |
| 69 | GCCTCCCTCGCGCCATCAG | TCACGT | AGAGTTTGATCMTGGCTCAG |
| 70 | GCCTCCCTCGCGCCATCAG | TCACTC | AGAGTTTGATCMTGGCTCAG |
| 71 | GCCTCCCTCGCGCCATCAG | TCAGTC | AGAGTTTGATCMTGGCTCAG |
| 72 | GCCTCCCTCGCGCCATCAG | TCATGT | AGAGTTTGATCMTGGCTCAG |
| 73 | GCCTCCCTCGCGCCATCAG | TCGAGT | AGAGTTTGATCMTGGCTCAG |
| 74 | GCCTCCCTCGCGCCATCAG | TCGATC | AGAGTTTGATCMTGGCTCAG |
| 75 | GCCTCCCTCGCGCCATCAG | TCGCGT | AGAGTTTGATCMTGGCTCAG |
| 76 | GCCTCCCTCGCGCCATCAG | TCGCTC | AGAGTTTGATCMTGGCTCAG |
| 77 | GCCTCCCTCGCGCCATCAG | TCGTGT | AGAGTTTGATCMTGGCTCAG |
| 78 | GCCTCCCTCGCGCCATCAG | TCTAGT | AGAGTTTGATCMTGGCTCAG |
| 79 | GCCTCCCTCGCGCCATCAG | TCTATC | AGAGTTTGATCMTGGCTCAG |
| 80 | GCCTCCCTCGCGCCATCAG | TCTCGT | AGAGTTTGATCMTGGCTCAG |
| 81 | GCCTCCCTCGCGCCATCAG | TCTCTC | AGAGTTTGATCMTGGCTCAG |
| 82 | GCCTCCCTCGCGCCATCAG | TCTGTC | AGAGTTTGATCMTGGCTCAG |
| 83 | GCCTCCCTCGCGCCATCAG | AGACAG | AGAGTTTGATCMTGGCTCAG |
| 84 | GCCTCCCTCGCGCCATCAG | AGAGAG | AGAGTTTGATCMTGGCTCAG |
| 85 | GCCTCCCTCGCGCCATCAG | AGATAG | AGAGTTTGATCMTGGCTCAG |
| 86 | GCCTCCCTCGCGCCATCAG | AGCGAG | AGAGTTTGATCMTGGCTCAG |
| 87 | GCCTCCCTCGCGCCATCAG | AGCTAG | AGAGTTTGATCMTGGCTCAG |
| 88 | GCCTCCCTCGCGCCATCAG | AGTCAG | AGAGTTTGATCMTGGCTCAG |
| 89 | GCCTCCCTCGCGCCATCAG | AGTGAG | AGAGTTTGATCMTGGCTCAG |
| 90 | GCCTCCCTCGCGCCATCAG | ATACAG | AGAGTTTGATCMTGGCTCAG |
| 91 | GCCTCCCTCGCGCCATCAG | ATAGAG | AGAGTTTGATCMTGGCTCAG |
| 92 | GCCTCCCTCGCGCCATCAG | ATATAG | AGAGTTTGATCMTGGCTCAG |
| 93 | GCCTCCCTCGCGCCATCAG | ATCGAG | AGAGTTTGATCMTGGCTCAG |
| 94 | GCCTCCCTCGCGCCATCAG | ATCTAG | AGAGTTTGATCMTGGCTCAG |
| 95 | GCCTCCCTCGCGCCATCAG | ATGCAG | AGAGTTTGATCMTGGCTCAG |
| 96 | GCCTCCCTCGCGCCATCAG | ATGTAG | AGAGTTTGATCMTGGCTCAG |

FIGURE 7C

REVERSE TAGGED ADAPTER PRIMER

| Primer Pair | ADAPTER B | TAG | Reverse 16S rRNAPrimer |
|---|---|---|---|
| 1 | GCCTTGCCAGCCCGCTCAG | AGACGT | GCTGCCTCCCGTAGGAGT |
| 2 | GCCTTGCCAGCCCGCTCAG | AGACTC | GCTGCCTCCCGTAGGAGT |
| 3 | GCCTTGCCAGCCCGCTCAG | AGAGTC | GCTGCCTCCCGTAGGAGT |
| 4 | GCCTTGCCAGCCCGCTCAG | AGATGT | GCTGCCTCCCGTAGGAGT |
| 5 | GCCTTGCCAGCCCGCTCAG | AGCAGT | GCTGCCTCCCGTAGGAGT |
| 6 | GCCTTGCCAGCCCGCTCAG | AGCATC | GCTGCCTCCCGTAGGAGT |
| 7 | GCCTTGCCAGCCCGCTCAG | AGCGTC | GCTGCCTCCCGTAGGAGT |
| 8 | GCCTTGCCAGCCCGCTCAG | AGCTGT | GCTGCCTCCCGTAGGAGT |
| 9 | GCCTTGCCAGCCCGCTCAG | AGTAGT | GCTGCCTCCCGTAGGAGT |
| 10 | GCCTTGCCAGCCCGCTCAG | AGTATC | GCTGCCTCCCGTAGGAGT |
| 11 | GCCTTGCCAGCCCGCTCAG | AGTCGT | GCTGCCTCCCGTAGGAGT |
| 12 | GCCTTGCCAGCCCGCTCAG | AGTCTC | GCTGCCTCCCGTAGGAGT |
| 13 | GCCTTGCCAGCCCGCTCAG | AGTGTC | GCTGCCTCCCGTAGGAGT |
| 14 | GCCTTGCCAGCCCGCTCAG | ATACGT | GCTGCCTCCCGTAGGAGT |
| 15 | GCCTTGCCAGCCCGCTCAG | ATACTC | GCTGCCTCCCGTAGGAGT |
| 16 | GCCTTGCCAGCCCGCTCAG | ATAGTC | GCTGCCTCCCGTAGGAGT |
| 17 | GCCTTGCCAGCCCGCTCAG | ATATGT | GCTGCCTCCCGTAGGAGT |
| 18 | GCCTTGCCAGCCCGCTCAG | ATCAGT | GCTGCCTCCCGTAGGAGT |
| 19 | GCCTTGCCAGCCCGCTCAG | ATCATC | GCTGCCTCCCGTAGGAGT |
| 20 | GCCTTGCCAGCCCGCTCAG | ATCGTC | GCTGCCTCCCGTAGGAGT |
| 21 | GCCTTGCCAGCCCGCTCAG | ATCTGT | GCTGCCTCCCGTAGGAGT |
| 22 | GCCTTGCCAGCCCGCTCAG | ATGAGT | GCTGCCTCCCGTAGGAGT |
| 23 | GCCTTGCCAGCCCGCTCAG | ATGATC | GCTGCCTCCCGTAGGAGT |
| 24 | GCCTTGCCAGCCCGCTCAG | ATGCGT | GCTGCCTCCCGTAGGAGT |
| 25 | GCCTTGCCAGCCCGCTCAG | ATGCTC | GCTGCCTCCCGTAGGAGT |
| 26 | GCCTTGCCAGCCCGCTCAG | ATGTGT | GCTGCCTCCCGTAGGAGT |
| 27 | GCCTTGCCAGCCCGCTCAG | CACAGT | GCTGCCTCCCGTAGGAGT |
| 28 | GCCTTGCCAGCCCGCTCAG | CACATC | GCTGCCTCCCGTAGGAGT |
| 29 | GCCTTGCCAGCCCGCTCAG | CACGTC | GCTGCCTCCCGTAGGAGT |
| 30 | GCCTTGCCAGCCCGCTCAG | CACTGT | GCTGCCTCCCGTAGGAGT |
| 31 | GCCTTGCCAGCCCGCTCAG | CAGAGT | GCTGCCTCCCGTAGGAGT |
| 32 | GCCTTGCCAGCCCGCTCAG | CAGATC | GCTGCCTCCCGTAGGAGT |
| 33 | GCCTTGCCAGCCCGCTCAG | CAGCGT | GCTGCCTCCCGTAGGAGT |
| 34 | GCCTTGCCAGCCCGCTCAG | CAGCTC | GCTGCCTCCCGTAGGAGT |
| 35 | GCCTTGCCAGCCCGCTCAG | CAGTGT | GCTGCCTCCCGTAGGAGT |
| 36 | GCCTTGCCAGCCCGCTCAG | CATAGT | GCTGCCTCCCGTAGGAGT |
| 37 | GCCTTGCCAGCCCGCTCAG | CATATC | GCTGCCTCCCGTAGGAGT |
| 38 | GCCTTGCCAGCCCGCTCAG | CATCGT | GCTGCCTCCCGTAGGAGT |
| 39 | GCCTTGCCAGCCCGCTCAG | CATCTC | GCTGCCTCCCGTAGGAGT |
| 40 | GCCTTGCCAGCCCGCTCAG | CATGTC | GCTGCCTCCCGTAGGAGT |
| 41 | GCCTTGCCAGCCCGCTCAG | CGACGT | GCTGCCTCCCGTAGGAGT |
| 42 | GCCTTGCCAGCCCGCTCAG | CGACTC | GCTGCCTCCCGTAGGAGT |
| 43 | GCCTTGCCAGCCCGCTCAG | CGAGTC | GCTGCCTCCCGTAGGAGT |
| 44 | GCCTTGCCAGCCCGCTCAG | CGATGT | GCTGCCTCCCGTAGGAGT |
| 45 | GCCTTGCCAGCCCGCTCAG | CGCAGT | GCTGCCTCCCGTAGGAGT |
| 46 | GCCTTGCCAGCCCGCTCAG | CGCATC | GCTGCCTCCCGTAGGAGT |
| 47 | GCCTTGCCAGCCCGCTCAG | CGCGTC | GCTGCCTCCCGTAGGAGT |
| 48 | GCCTTGCCAGCCCGCTCAG | CGCTGT | GCTGCCTCCCGTAGGAGT |
| 49 | GCCTTGCCAGCCCGCTCAG | CGTAGT | GCTGCCTCCCGTAGGAGT |
| 50 | GCCTTGCCAGCCCGCTCAG | CGTATC | GCTGCCTCCCGTAGGAGT |

FIGURE 7D

REVERSE TAGGED ADAPTER PRIMER

| Primer Pair | ADAPTER B | TAG | Reverse 16S rRNAPrimer |
|---|---|---|---|
| 51 | GCCTTGCCAGCCCGCTCAG | CGTCGT | GCTGCCTCCCGTAGGAGT |
| 52 | GCCTTGCCAGCCCGCTCAG | CGTCTC | GCTGCCTCCCGTAGGAGT |
| 53 | GCCTTGCCAGCCCGCTCAG | CGTGCA | GCTGCCTCCCGTAGGAGT |
| 54 | GCCTTGCCAGCCCGCTCAG | CGTGTC | GCTGCCTCCCGTAGGAGT |
| 55 | GCCTTGCCAGCCCGCTCAG | TACAGT | GCTGCCTCCCGTAGGAGT |
| 56 | GCCTTGCCAGCCCGCTCAG | TACATC | GCTGCCTCCCGTAGGAGT |
| 57 | GCCTTGCCAGCCCGCTCAG | TACGTC | GCTGCCTCCCGTAGGAGT |
| 58 | GCCTTGCCAGCCCGCTCAG | TACTGT | GCTGCCTCCCGTAGGAGT |
| 59 | GCCTTGCCAGCCCGCTCAG | TAGAGT | GCTGCCTCCCGTAGGAGT |
| 60 | GCCTTGCCAGCCCGCTCAG | TAGATC | GCTGCCTCCCGTAGGAGT |
| 61 | GCCTTGCCAGCCCGCTCAG | TAGCGT | GCTGCCTCCCGTAGGAGT |
| 62 | GCCTTGCCAGCCCGCTCAG | TAGCTC | GCTGCCTCCCGTAGGAGT |
| 63 | GCCTTGCCAGCCCGCTCAG | TAGTGT | GCTGCCTCCCGTAGGAGT |
| 64 | GCCTTGCCAGCCCGCTCAG | TATAGT | GCTGCCTCCCGTAGGAGT |
| 65 | GCCTTGCCAGCCCGCTCAG | TATATC | GCTGCCTCCCGTAGGAGT |
| 66 | GCCTTGCCAGCCCGCTCAG | TATCGT | GCTGCCTCCCGTAGGAGT |
| 67 | GCCTTGCCAGCCCGCTCAG | TATCTC | GCTGCCTCCCGTAGGAGT |
| 68 | GCCTTGCCAGCCCGCTCAG | TATGTC | GCTGCCTCCCGTAGGAGT |
| 69 | GCCTTGCCAGCCCGCTCAG | TCACGT | GCTGCCTCCCGTAGGAGT |
| 70 | GCCTTGCCAGCCCGCTCAG | TCACTC | GCTGCCTCCCGTAGGAGT |
| 71 | GCCTTGCCAGCCCGCTCAG | TCAGTC | GCTGCCTCCCGTAGGAGT |
| 72 | GCCTTGCCAGCCCGCTCAG | TCATGT | GCTGCCTCCCGTAGGAGT |
| 73 | GCCTTGCCAGCCCGCTCAG | TCGAGT | GCTGCCTCCCGTAGGAGT |
| 74 | GCCTTGCCAGCCCGCTCAG | TCGATC | GCTGCCTCCCGTAGGAGT |
| 75 | GCCTTGCCAGCCCGCTCAG | TCGCGT | GCTGCCTCCCGTAGGAGT |
| 76 | GCCTTGCCAGCCCGCTCAG | TCGCTC | GCTGCCTCCCGTAGGAGT |
| 77 | GCCTTGCCAGCCCGCTCAG | TCGTGT | GCTGCCTCCCGTAGGAGT |
| 78 | GCCTTGCCAGCCCGCTCAG | TCTAGT | GCTGCCTCCCGTAGGAGT |
| 79 | GCCTTGCCAGCCCGCTCAG | TCTATC | GCTGCCTCCCGTAGGAGT |
| 80 | GCCTTGCCAGCCCGCTCAG | TCTCGT | GCTGCCTCCCGTAGGAGT |
| 81 | GCCTTGCCAGCCCGCTCAG | TCTCTC | GCTGCCTCCCGTAGGAGT |
| 82 | GCCTTGCCAGCCCGCTCAG | TCTGTC | GCTGCCTCCCGTAGGAGT |
| 83 | GCCTTGCCAGCCCGCTCAG | AGAGCA | GCTGCCTCCCGTAGGAGT |
| 84 | GCCTTGCCAGCCCGCTCAG | AGATCA | GCTGCCTCCCGTAGGAGT |
| 85 | GCCTTGCCAGCCCGCTCAG | AGCACA | GCTGCCTCCCGTAGGAGT |
| 86 | GCCTTGCCAGCCCGCTCAG | AGCGCA | GCTGCCTCCCGTAGGAGT |
| 87 | GCCTTGCCAGCCCGCTCAG | AGCTCA | GCTGCCTCCCGTAGGAGT |
| 88 | GCCTTGCCAGCCCGCTCAG | AGTACA | GCTGCCTCCCGTAGGAGT |
| 89 | GCCTTGCCAGCCCGCTCAG | AGTGCA | GCTGCCTCCCGTAGGAGT |
| 90 | GCCTTGCCAGCCCGCTCAG | ATAGCA | GCTGCCTCCCGTAGGAGT |
| 91 | GCCTTGCCAGCCCGCTCAG | ATATCA | GCTGCCTCCCGTAGGAGT |
| 92 | GCCTTGCCAGCCCGCTCAG | ATCACA | GCTGCCTCCCGTAGGAGT |
| 93 | GCCTTGCCAGCCCGCTCAG | ATCGCA | GCTGCCTCCCGTAGGAGT |
| 94 | GCCTTGCCAGCCCGCTCAG | ATCTCA | GCTGCCTCCCGTAGGAGT |
| 95 | GCCTTGCCAGCCCGCTCAG | ATGACA | GCTGCCTCCCGTAGGAGT |
| 96 | GCCTTGCCAGCCCGCTCAG | ATGTCA | GCTGCCTCCCGTAGGAGT |

MULTITAG SEQUENCING ECOGENOMICS ANALYSIS

RELATED APPLICATIONS

This application is a continuation of U.S. patent application Ser. No. 14/066,967 filed Oct. 30, 2013 (now U.S. Pat. No. 9,453,262), which is a divisional of U.S. patent application Ser. No. 12/515,262 filed May 15, 2009 (now U.S. Pat. No. 8,603,749), which is a National Stage of PCT/US07/84840, filed Nov. 15, 2007, which claims the full benefit of and priority to U.S. provisional application No. 60/858,948, filed on 15 Nov. 2006, each of which is hereby incorporated by reference in its entirety.

STATEMENT OF GOVERNMENT RIGHTS

Work described herein was done partly with Government support under Grant No. 1R43DK074275-01A2 awarded by the U.S. National Institute of Diabetes and Digestive and Kidney Diseases, and the US Government therefore may have certain rights in the invention.

FIELD OF THE INVENTION

The invention relates to the determination of polynucleotide sequences. It also relates to determining sequences in multiple samples, in some particulars in multiple environmental samples and in multiple clinical samples.

BACKGROUND

Sequence determination technologies for proteins, RNAs and DNAs, have been pivotal in the development of modern molecular biology. During the past fifteen years, DNA sequencing in particular has been the core technology in an on-going revolution in the scope and the depth of understanding of genomic organization and function. The on-going development of sequencing technology is, perhaps, best symbolized by the determination of the complete sequence of a human genome.

The human genome sequencing project served a number of purposes. It served as a platform for programmatic development of improved sequencing technologies and of genome sequencing efforts. It also served to provide a framework for the production and distribution of sequencing information from increasingly large scale sequencing projects. These projects provided complete genome sequences for a succession of model organisms of increasingly large genetic complements. These accomplishments, culminating in the completion of a human genome sequence, highlight the very considerable power and throughput of contemporary sequencing technology.

At the same time, however, they highlight the limitations of current technology and the need for considerable improvements in speed, accuracy, and cost before sequencing can be fully exploited in research and medicine. Among the areas that can be seen most readily to require advances in sequencing technology are clinical sequencing applications that require whole genome information, environmental applications involving multiple organisms in mixtures, and applications that require processing of many samples. These are, of course, just a few among a great many areas that either require or will benefit greatly from more capable and less expensive sequencing methods.

To date, virtually all sequencing has been done by Sanger chain elongation methods. All Sanger methods require separating the elongation products with single base resolution. Currently, while PAGE still is used for this purpose in some commercial sequencers, capillary electrophoresis is the method of choice for high throughput DNA sequencers. Both gel-based and capillary-based separation methods are time consuming, costly, and limit throughput. Chip based methods, such as Affymetrix GeneChips and HySeq's sequencing by hybridization methods, require chips that can be produced only by capital intensive and complex manufacturing processes. These limitations pose obstacles to the utilization of sequencing for many purposes, such as those described above. Partly to overcome the limitations imposed by the necessity for powerful separation techniques in chain termination sequencing methods and the manufacturing requirements of chip-based methods, a number of technologies are currently being developed that do not require the separation of elongation products with integer resolution and do not require chips.

A lead technology of this type is a bead, emulsion amplification, and pyrosequencing-based method developed by 454 Life Sciences. (See Marguilles, et al. (2005) Nature 437: 376, which is incorporated herein by reference in its entirety, particularly as to the afore-mentioned methods. The method utilizes a series of steps to deposit single, amplified DNA molecules in individual wells of a plate containing several million picoliter wells. The steps ensure that each well of the plate either contains no DNA or the amplified DNA from a single original molecule. Pyrosequencing is carried out in the wells by elongation of a primer template in much the same way as Sanger sequencing. Pyrosequencing does not involve chain termination and does not require separation of elongation products. Instead sequencing proceeds stepwise by single base addition cycles. In each cycle one of the four bases—A, T, G, or C—is included in the elongation reaction. The other three bases are omitted. A base is added to the growing chain if it is complementary to the next position on the template. Light is produced whenever a base is incorporated into the growing complimentary sequence. By interrogating with each of A, C, G, or T in succession, the identity of the base at each position can be determined. Sequencing reactions are carried out in many wells simultaneously. Signals are collected from all the wells at once using an imaging detector. Thus, a multitude of sequences can be determined at the same time.

In principle, each well containing a DNA will emit a signal for only one of the four bases for each position. In practice, runs of the same base at two or more positions in succession lead to the emission of proportionally stronger signals for the first position in the run. Consequently, reading out the sequence from a given well is a bit more complicated then simply noting, for each position, which of the four bases is added. Nevertheless, because signals are proportional to the number of incorporations, sequences can be accurately reconstructed from the signal strength for most runs.

The technology has been shown to read accurately an average of about 250 or so bases per well with acceptable accuracy. A device offered by 454 Life Sciences currently uses a 6.4 $cm^2$ picoliter well "plate" containing 1,600,000 picoliter sized wells for sequencing about 400,000 different templates. The throughput for a single run using this plate currently is about 100 million bases in four hours. Even though this is a first generation device, its throughput is nearly 100 times better than standard Sanger sequencing devices.

Numerous other methods are being developed for ultra high throughput sequencing by other institutions and companies. Sequencing by synthesis methods that rely on target amplification are being developed and/or commercialized by George Church at Harvard University, by Solexa, and by others. Ligation sequencing methods have been developed and/or are being commercialized by Applied Biosystems and Solexa, among others. Array and hybridization sequencing methods are commercially available and/or are being developed by Affymetrix, Hyseq, Biotrove, Nimblegen, Illumina, and others. Methods of sequencing single molecules are being pursued by Helicos based on sequencing by synthesis and U.S. Genomics (among others) based on poration.

These methods represent a considerable improvement in throughput over past methods, in some regards. And they promise considerable improvement in economy as well. However, currently they are expensive to implement and use, they are limited to relatively short reads and, although massively parallel, they have limitations that must be overcome to realize their full potential.

One particular disadvantage of these methods, for example, is that samples must be processed serially, reducing throughput and increasing cost. This is a particularly great disadvantage when large numbers of samples are being processed, such as may be the case in clinical studies and environmental sampling, to name just two applications.

The incorporation of indexing sequences by ligation to random shotgun libraries has been disclosed in U.S. Pat. Nos. 7,264,929, 7,244,559, and 7,211,390, but the direct ligation methods therein disclosed distort the distribution of the components within the samples (as illustrated in FIG. 4 herein) and therefore are inappropriate for enumerating components within each sample.

Accordingly, there is a need to improve sample throughput, to lower the costs of sequencing polynucleotides from many samples at a time, and to accurately enumerate the components of samples analyzed by high throughput, parallelized and multiplex techniques.

SUMMARY

It is therefore an object of the present invention to provide sequencing methods with improved sample throughput. The following paragraphs describe a few illustrative embodiments of the invention that exemplify some of its aspects and features. They are not exhaustive in illustrating its many aspects and embodiments, and thus are not in any way limitative of the invention. Many other aspects, features, and embodiments of the invention are described herein. Many other aspects and embodiments will be readily apparent to those skilled in the art upon reading the application and giving it due consideration in the full light of the prior art and knowledge in the field.

Embodiments provide multiplex methods for the quantitative determination of polynucleotides in two or more samples, comprising:

hybridizing a first primer to polynucleotides in a first sample, said first primer comprising a first tag sequence and a first probe sequence specific for a first target sequence, wherein said first target sequence is 3' to a variable genetic region;

elongating primer templates formed thereby to form a first population of tagged polynucleotides comprising: said first primer including said first tag sequence; and sequences of said variable genetic region;

hybridizing a second primer to polynucleotides in a second sample, said second primer comprising a second tag sequence and a second probe sequence specific for a second target sequence, wherein said second target sequence is 3' to the same variable genetic region as said first target sequence, wherein further said second probe sequence may be the same as or different from said first probe sequence;

elongating primer templates formed thereby to form a second population of tagged polynucleotides comprising: said second primer including said second tag sequence; and sequences of said variable genetic region;

mixing said first and second populations together;

determining sequences of polynucleotides comprising tag sequences and the sequences of the variable genetic element in said mixture;

from the tag sequences comprised in the polynucleotide sequences thus determined identifying the sample in which polynucleotide sequences occurred;

from the sequences of the variable genetic region comprised in the polynucleotide sequences thus determined identifying particular variants of said variable genetic element;

from this information determining the number of time one or more given variants occur in each sample, and from the number for each variant in the polynucleotides thus determined, quantifying said polynucleotides in said samples;

wherein said sequences are determined without Southern blot transfer and/or without size-separating primer extension products and/or without electrophoresis.

Embodiments provide multiplex methods for the quantitative determination of polynucleotides in two or more samples, comprising:

hybridizing a first primer pair to polynucleotides in a first sample, the first primer of said first primer pair comprising a first tag sequence and a first probe sequences specific for a first target sequence and the second primer of said first primer pair comprising a second tag sequence and a second probe sequence specific for a second target sequence, wherein the first and the second probe sequences flank and hybridize to opposite strands of a variable genetic region;

elongating primer templates formed thereby to from a first population of tagged polynucleotides, each of said polynucleotides comprising: (a) the sequence of said first primer of said first primer pair, a sequence of said variable genetic region, and a sequence complementary to the sequence of said second primer of said first primer pair or (b) a sequence complementary to the sequence of said first primer of said first primer pair, a sequence of said variable genetic region and the sequence of said second primer of said first primer pair;

hybridizing a second primer pair to polynucleotides in a second sample, the first primer of said second primer pair comprising a third tag sequence and said first probe sequences specific for said first target sequence and the second primer of said second primer pair comprising a fourth tag sequence and said second probe sequence specific for said second target sequence;

elongating primer templates formed thereby to from a second population of tagged polynucleotides, each of said polynucleotides comprising: (a) the sequence of said first primer of said second primer pair, a sequence of said variable genetic region, and a sequence complementary to the sequence of said second primer of said second primer pair or (b) a sequence complementary to the sequence of said first primer of said second primer pair, a sequence of said variable genetic region and the sequence of said second primer of said second primer pair;

mixing said first and second populations together;

determining sequences of polynucleotides in said mixture, comprising the tag sequences and the variable genetic element;

from the tag sequences comprised in the polynucleotide sequences thus determined identifying the sample in which polynucleotide sequences occurred;

from the sequences of the variable genetic region comprised in the polynucleotide sequences thus determined identifying particular variants of said variable genetic element;

from this information determining the number of times given variants occur in each sample, and from the number for each variant in the polynucleotides thus determined, quantifying said polynucleotides in said samples.

wherein said sequences are determined without Southern blot transfer and/or without size-separating primer extension products and/or without electrophoresis.

Embodiments provide methods in accordance with any of the foregoing or the following wherein given polynucleotide sequences in a sample is quantified by a method comprising normalizing the number occurrences determined for the given sequence. In embodiments the number of occurrences is normalized by dividing the number of occurrences determined for the given polynucleotide sequence by the total number of occurrences of polynucleotide sequences in the sample. In embodiments the given polynucleotide sequences is that of a given variant of a variable genetic region and, in embodiments, the quantity of the given variant in the sample is normalized by dividing the number of occurrences of that variant by the total number of occurrences of all variants of the variable genetic region in the sample.

Embodiments provide a multiplex method for determining polynucleotide sequences in two or more samples, comprising: attaching a first tag sequence to one or more polynucleotides of a first sample; attaching a second tag sequence different from said first tag sequence to one or more polynucleotides of a second sample; mixing the tagged polynucleotides of said first and second samples together; determining sequences of said polynucleotides comprising said first and said second tags; and identifying said first and second tags in said sequences; thereby identifying sequences of said polynucleotides of said first sample and second samples, wherein said sequences are determined without Southern blot transfer and/or without size-separating primer extension products and/or without electrophoresis.

Embodiments provide a multiplex method for determining polynucleotide sequences in two or more samples comprising:

attaching a first tag sequence, $t_1$, to $P_{1-1}$ through $P_{1-n1}$ polynucleotides in a first sample, thereby to provide a first plurality of polynucleotides tagged with said first tag, tiPii through $t_1 P_{1-n1}$;

attaching a second tag sequence, $t_2$, to $P_{2-1}$ through $P_{2-n2}$ polynucleotides in a second sample, thereby to provide a second plurality of polynucleotides tagged with said second tag, $t_2 P_{2-1}$ through $t_2 P_{2-n2}$;

mixing together said polynucleotides tagged with said first and said second tags;

determining sequences of polynucleotides comprising said tags in said mixture;

identifying said first and second tags in said sequences and;

by said first tag identifying polynucleotide sequences of said first sample and by said second tag identifying polynucleotide sequences of said second sample;

wherein said sequences are determined without Southern blot transfer and/or without size-separating primer extension products and/or without electrophoresis.

Embodiments provide a method according to any of the foregoing or the following, wherein the number of said polynucleotides in said first sample, n1, is any of 2, 5, 10, 25, 50, 100, 150, 200, 250, 500, 1,000, 1,500, 2,000, 2,500, 5,000, 7,500, 10,000, 12,500, 15,000, 17,500, 20,000, 25,000, 30,000, 35,000, 40,000, 50,000, 75,000, 100,000, 150,000, 200,000, 250,000, 500,000, 1,000,000 or more, and the number of said polynucleotides in said second sample, $n_2$, is any of 2, 5, 10, 25, 50, 100, 150, 200, 250, 500, 1,000, 1,500, 2,000, 2,500, 5,000, 7,500, 10,000, 12,500, 15,000, 17,500, 20,000, 25,000, 30,000, 35,000, 40,000, 50,000, 75,000, 100,000, 150,000, 200,000, 250,000, 500,000, 1,000,000 or more.

Embodiments provide a method according to any of the foregoing or the following, wherein the number of said samples and of said different tags therefor is 5, 10, 15, 20, 25, 50, 75, 100, 150, 200, 250, 500, 1,000, 2,500, 5,000, 10,000 or more.

Embodiments provide a method according to any of the foregoing or the following, wherein the tags are nucleotide sequences that are 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 nucleotides long or any combination thereof.

Embodiments provide a method according to any of the foregoing or the following, wherein the tags are incorporated into said polynucleotides by a step of ligation, provided that the step of ligation does not result in biasing.

Embodiments provide a method according to any of the foregoing or the following, wherein the tags are incorporated into said polynucleotides by a step of ligation and/or by a step of amplification.

Embodiments provide a method according to any of the foregoing or the following, wherein said tags are comprised in primers for amplification and are incorporated into said polynucleotides by amplification using said primers.

Embodiments provide a method according to any of the foregoing or the following, wherein said tags are incorporated into said polynucleotides by a process comprising a step of cloning into a vector.

Embodiments provide a method according to any of the foregoing or the following, wherein the tags are comprised in adapters for amplification and said adapters are ligated to polynucleotides in said samples. Embodiments provide a method in this regard, wherein further, said polynucleotides ligated thereby to said tags are amplified via said adapters. Embodiments provide a method in this regard, wherein further, said adapters comprise a moiety for immobilization. In embodiments said moiety is a ligand; in embodiments it is biotin. Embodiments provide a method in this regard, wherein further, said tags are comprised on adapters for bead emulsion amplification. In embodiments the adapters are suitable for use in a sequencing system of 454 Life Sciences or other sequencing system in which bead emulsion amplification is carried out.

Embodiments provide a method according to any of the foregoing or the following, wherein the primer for amplification comprises a sequence for PCR amplification, linear amplification, transcriptional amplification, rolling circle replication, or QB replication.

Embodiments provide a method according to any of the foregoing or the following, wherein the primer for amplification comprises a sequence for PCR amplification.

Embodiments provide a method according to any of the foregoing or the following, wherein each of said polynucleotides is disposed individually on a bead isolated from other polynucleotides.

Embodiments provide a method according to any of the foregoing or the following, wherein each of said polynucleotides is disposed individually on a bead isolated from other said polynucleotides, is amplified while disposed therein, and the amplification products thereof also are disposed on said bead.

Embodiments provide a method according to any of the foregoing or the following, wherein each of said polynucleotides is disposed individually on a bead isolated from other said polynucleotides, is amplified while disposed therein, the amplification products thereof also are disposed on said bead, and each said bead is disposed individually in a well isolated from other said beads.

Embodiments provide a method according to any of the foregoing or the following, wherein the sequences are determined by pyrosequencing.

Embodiments provide a method according to any of the foregoing or the following, wherein said samples are biological samples, each comprising one or more species.

Embodiments provide a method according to any of the foregoing or the following, wherein at least one sequence of said polynucleotides is specific to a particular organism.

Embodiments provide a method according to any of the foregoing or the following, wherein said sequences comprise a variable 16S rRNA sequence.

Embodiments provide a method according to any of the foregoing or the following, wherein said sequences comprise a variable 18S rRNA sequence, a variable rRNA ITS sequence, a mitochondrial sequence, a microsatellite sequence, a metabolic enzyme sequence, and/or a genetic disease sequence.

Embodiments provide a method according to any of the foregoing or the following, wherein the samples are microbial community samples.

Embodiments provide a method according to any of the foregoing or the following, wherein the samples are microbial community samples for clinical analysis of a patient.

Embodiments provide a method according to any of the foregoing or the following, wherein the samples are microbial community environmental samples.

Embodiments provide a method according to any of the foregoing or the following, wherein the samples are microbial community soil samples.

Embodiments provide a method according to any of the foregoing or the following, wherein the samples are microbial community water samples.

Embodiments provide a method according to any of the foregoing or the following, wherein the samples are samples for SNP analysis.

Embodiments provide a method according to any of the foregoing or the following, wherein the samples are samples for genotyping.

Embodiments provide a multiplex method according to any of the foregoing or the following for determining polynucleotide sequences of two or more samples, comprising, amplifying polynucleotides of a first sample to produce first amplified polynucleotides comprising a first tag sequence;

separately amplifying polynucleotides of a second sample to produce second amplified polynucleotides comprising a second tag sequence different from said first tag sequence;

wherein the amplification products arising from different individual polynucleotides are spatially separated from one another;

mixing together amplicons of said first and second samples;

distributing the amplicons in the mixture into spatially distinct locations; sequencing the amplicons thus distributed using one or more primers that hybridize 5' to said tag sequences;

identifying said tag sequences in the sequences of polynucleotides thus determined; and identifying by said tags polynucleotides of said first sample and polynucleotides of said second sample.

Embodiments provide a method according to any of the foregoing or the following, comprising, (a) for each sample separately: isolating polynucleotides to be sequenced, ligating said polynucleotides to a common adaptor comprising a tag sequence, and capturing individual ligated polynucleotides onto individual beads under conditions that provide predominately for the immobilization of 0 or 1 molecule per bead;

(b) thereafter mixing together said beads comprising said polynucleotides.

Embodiments provide a method according to any of the foregoing or the following, further comprising, amplifying bead-immobilized polynucleotides in droplets of an emulsion thereby to clonally amplify said individual polynucleotides on said beads, wherein amplification comprises amplification of said tag sequence.

Embodiments provide a method according to any of the foregoing or the following, further comprising, distributing individual droplets containing said amplified polynucleotides into wells under conditions that provide predominantly for 0 or 1 droplet per well, determining in individual wells the sequences of polynucleotides comprising said tag sequences, and by said tag sequences identifying polynucleotides of said first and said second samples.

In embodiments the invention provides methods in accordance with any of the foregoing or the following, for any one or more of detecting, monitoring, profiling, prognosticating, and/or diagnosing a disorder, disease, or the like.

In embodiments the invention provides methods in accordance with any of the foregoing or the following, for analyzing the composition, diversity, stability, dynamics, and/or changes in agricultural, food, biosecurity, veterinary, clinical, ecological, zoological, oceanological, and/or any other sample comprising one or more polynucleotides.

Embodiments provide kits comprising a plurality of two or more primers, each primer in said plurality comprising a tag sequence and a probe sequence specific to a target sequence, wherein:

(A) in each of said primers the probe sequence is 3' to the tag sequence, but not necessarily adjacent thereto;

(B) in each of said primers: the tag sequence is different from the tag sequence of the other in the plurality; the tag sequence is not the complementary sequence to any other tag sequence in the plurality; the tag sequence does not contain any homodinucleotide sequences; the junction sequences between the tag sequence and the adjacent parts of the primer, if any, is not a homodinucleotide sequence;

(C) in each of said primers the probe sequence is complementary to the target sequence and the target sequence is located 3' to a variable genetic region, and (D) each of said primers is disposed separately from the others in containers in said kit.

Embodiments provide kits in accordance with any of the foregoing or the following, wherein each of said primers further comprises a priming sequence 5' to the tag sequence but not necessarily adjacent thereto, and the priming sequence is the same in all of said primers, said kit further comprising a primer complementary to and effective for polymerization from said priming sequence.

Embodiments provides kits comprising a plurality of two or more primers pairs, each primer in said plurality comprising a tag sequence and a probe sequence specific to a target sequence, wherein:

(A) in each of said primer the probe sequence is 3' to the tag sequence, but not necessarily adjacent thereto;

(B) in each of said primers: the tag sequence is different from the tag sequence of the other in the plurality; the tag sequence is not the complementary sequence to any other tag sequence in the plurality; the tag sequence does not contain any homodinucleotide sequences; the junction sequences between the tag sequence and the adjacent parts of the primer, if any, is not a homodinucleotide sequence;

(C) in each of said primers the probe sequence is complementary to the target sequence, (D) in each primer pair the probe sequences are specific to target sequences that flank a variable genetic region;

(E) each of said primers is disposed separately from the others in said kit.

Embodiments provides kits in accordance with any of the foregoing or the following, wherein, the primers further comprise a priming sequence 5' to the tag sequence but not necessarily adjacent thereto, the priming sequence either is the same in all the primers, or one member of each pair has the same first priming sequence and the second member of each pair has the same second priming sequence, said kit further comprising disposed separately from one another in one or more containers one or more primers complementary to and effective for elongation from said priming.

Embodiments provide a kit useful in methods according to any of the foregoing or the following, comprising a set of primers and/or adapters, wherein each primer and/or adapter in said set comprises a tag sequence and a primer sequence. In embodiments the primers and/or adapters further comprise a moiety for immobilization. In embodiments the primers and/or adapters comprise biotin. In embodiments the primers and/or adapters in the set comprise all tag sequences defined by 2, 3, 4, 5, 6, 7, or 8 base polynucleotide sequences, wherein each of said primers and/or adapters are disposed in containers separate from one another. In embodiments there are 1-5, 3-10, 5-15, 10-25, 20-50, 25-75, 50-100, 50-150, 100-200, 150-500, 250-750, 100-1000, or more different tag sequences disposed separately from one another, so as to be useful for uniquely tagging said number of different samples. In embodiments the primers and/or adapters are suitable for use as 454 Life Sciences amplification adapters and/or primers. In embodiments the primers and/or adapters further comprise any one or more of a primer sequence for any one or more of a 16S rRNA sequence, an 18S rRNA sequence, an ITS sequence, a mitochondrial sequence, a microsatellite sequence, a metabolic enzyme sequence, a genetic disease sequence, and/or any other sequence for amplification or analysis.

In embodiments the invention provides a kit, in accordance with any of the foregoing or the following, comprising a set of primers and/or adapters for use in a method according to any of the foregoing or the following, wherein each primer and/or adapter in said set comprises a tag sequence, the tag sequence of each of said primers and/or adapters is different from that of the other primers and/or adapters in said set, the primers and/or adapters further comprise a priming sequence that is the same in all of the primers and/or adapters in said set, the tag sequences are located 5' to the priming sequence and the different primers and/or adapters comprising each different tag sequence are disposed separately from one another. In embodiments the tags are any number of bases long. In embodiments the tags are 2, 3, 4, 5, 6, 8, 10, 12 bases long. In embodiments the tags are 4 bases long. In embodiments the priming sequence is specific to any target polynucleotide of interest. In embodiments the priming sequence is specific to a sequence in 16S rRNA. In embodiments the tags differ from each other by at least 2 bases. In embodiments the tags do not contain polynucleotide tracts within the tag. In embodiments the tags do not contain homo-polynucleotide tracts within or at the junction of the tag and PCR primer. In embodiments the tags do not contain polynucleotide tracts within or at the junction of the tag and emulsion PCR adapter. In embodiments, the tags are not reverse compliments of each other.

BRIEF DESCRIPTION OF THE FIGURES

FIG. 2B is a diagram depicting the Emulsion PCR reaction beads randomly arrayed into picoliter plate. In step 2 in the process, the PCR products from all the samples are mixed, immobilized on beads, distributed into wells of the picoliter plate, and emulsion PCR amplified.

FIG. 2C is a diagram depicting the pyrosequencing process from each outside adapter in each well of the picoliter plate. Each reaction reads sequence from the adapter, through the unique tags and the associated sequence of the tagged sample.

FIG. 3 is the species distribution in (A) Controls, (B) Crohns, and (C) Ulcerative colitis samples determined by the 454 Life Science pyrosequencing process. Each bar in the histogram is the average normalized abundance of that taxa in each disease state. Each sample was run in a separate well on the picoliter plate using the 454 16 well mask.

FIG. 4A shows the size distribution of PCR amplicons in sample 309 before ligation and FIG. 4B shows the size distribution of sample 309 after ligation.

FIG. 5 is an example of the normalized taxa abundances in duplicate samples determined by Multitag pyrosequencing after direct ligation of the emulsion PCR adapters.

FIG. 6 shows all possible hexameric polynucleotide tags within which there are no dinucleotide repeats and no tag is the reverse complement of any other tag.

FIGS. 7A-D show 96 tagged adaptor primers in which there are no dinucleotide repeats in the tags, no dinucleotide repeats at the junction of the tags and the tags are not reverse complements of one another. In each case 5 bases of the primer also can be used to identify samples. 7A and 7B show the forward primers (SEQ ID NOS: 1-96, respectively in order of appearance). 7C and 7D show the reverse primers (SEQ ID NOS: 97-192, respectively in order of appearance).

GLOSSARY

Figure 1:
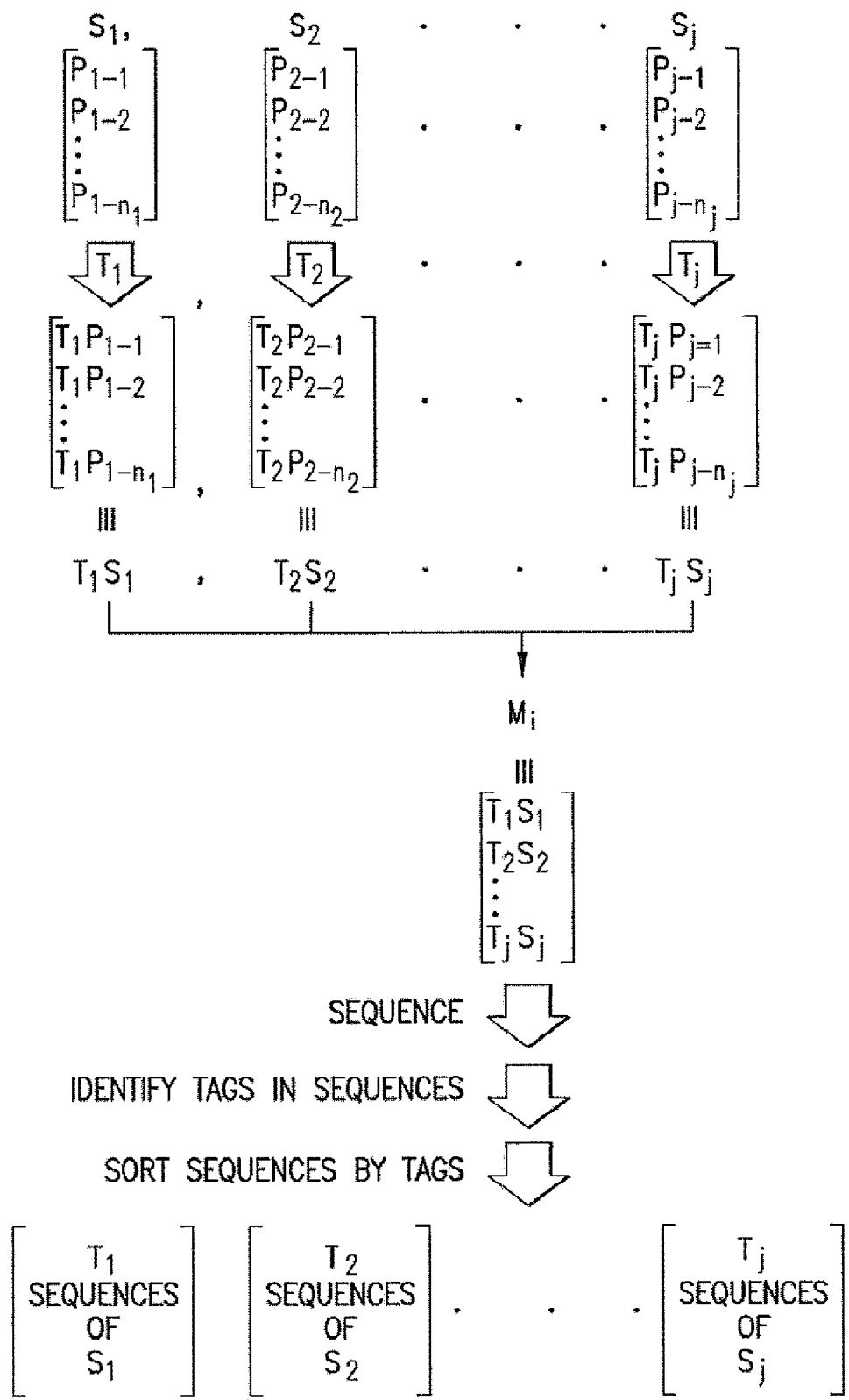
FIG. 1 is a schematic diagram showing a general embodiment of the invention. A plurality of samples ($S_1$, $S_2$, through $S_j$) is shown topmost in the Figure. Each sample is comprised of a plurality of polynucleotides ($P_{1-1}$ to $P_{1-n1}$ in $S_1$; $P_{2-1}$ to $P_{2-n2}$ in $S_2$; through $P_{j-1}$ to $P_{j-nj}$). The polynucleotides in each sample are labeled separately with a tag polynucleotide sequence, all the polynucleotides in a given sample being tagged (in this illustration) with a single tag sequence, designated in the figure as $T_1$ for $S_1$, $T_2$ for $S_2$, through $T_j$ for $S_j$. The individual tagged polynucleotides are denoted accordingly. The tagged polynucleotides in each sample are designated collectively, for each sample, $T_1S_1$, $T_2S_2$, through $T_jS_j$. The tagged polynucleotides from the samples are mixed together to form a mixture, designated M. The mixture is sequenced, typically by a massively parallel sequencing method. The tag sequences are identified in the data thus obtained. The sequences are grouped by tag. The sequences from the individual samples are thereby identified.

The meanings ascribed to various terms and phrases as used herein are illustratively explained below.

"A" or "an" means one or more; at least one.

"About" as used herein means roughly, approximately. Should a precise numerical definition be required, "about" means+/−25%.

"Adapter" means a polynucleotide sequence used to either attach single polynucleotide fragments to beads and/or to prime the emulsion PCR reaction and/or as a template to prime pyrosequencing reactions.

"ALH" is used herein to mean amplicon length heterogeneity.

"Amplicon" is used herein to refer to the products of an amplification reaction.

"Clonally amplified" is used herein generally to mean amplification of a single starting molecule. Typically it also refers to the clustering together of the amplification products, isolated from other amplification templates or products.

"dsDNA" means double stranded DNA.

Dysbiosis means a shift in a the species and abundance of species in a microbial community.

"Flanking" generally is used to mean on each side, such as on the 5' and the 3' side of a region of a polynucleotide— with reference to the 5' and the 3' ends of one or the other stand of a double stranded polynucleotide. Forward and reverse primers for amplifying a region of a polynucleotide by PCR, for instance, flank the region to be amplified.

"Microbial community sample" is used herein to refer to a sample, generally of a biological nature, containing two or more different microbes. Microbial community samples include, for instance, environmental samples, as well as biological samples, such as samples for clinical analysis. The term applies as well to preparations, such as DNA preparations, derived from such samples.

"Multiplex sequencing" herein refers to sequencing two or more types or samples of polynucleotides in a single reaction or in a single reaction vessel.

"PCO" means principal coordinates analysis.

"PCA" means principal component analysis.

"Picotiter plate" means a plate having a large number of wells that hold a relatively small volume, typically more wells than a 96-well microtiter plate, and smaller volumes than those of a typical 96-well microtiter plate well.

"Primer" means a polynucleotide sequence that is used to amplify PCR products and/or to prime sequencing reactions.

"ssDNA" means single stranded DNA.

"Tag," "Tag sequence," etc. means typically a heterologous sequence, such as a polynucleotide sequence that identifies another sequence with which it is associated as being of a given type or belonging to a given group.

"Variable genetic region" as used herein means a genetic region that varies, such as between individuals of a species and between species. The phrase does not denote a specific length, but, rather is used to denote a region comprising a variation the exact length of which may vary and may differ in different contexts. As to a double stranded polynucleotide, the term includes one or the other and both stands of the region, and may be used to refer to one, the other, or to both strands, and it will generally be clear from the context which is meant. A specific example of a genetic region that varies between individuals, provided for illustration only, is a genetic region that contains an SNP (single nucleotide polymorphism) site. By variable genetic region in this regard is meant a region containing the SNP site. Different sequences of the SNP in this regard constitute the variants of the variable genetic region. A specific example of a variable genetic region that differs between species is the genes for 16S RNA which vary characteristically between microbes and can be used to identify microbes in mixed community samples as described in greater detail in some of the examples herein.

DESCRIPTION OF THE INVENTION

In certain aspects and embodiments the invention relates to multiplex sequencing analysis using tags. In various aspects and embodiments of the invention in this regard the invention provides methods for sequencing two or more samples simultaneously in a mixture with one another, wherein each sample is first linked to a sample-specific sequence tag, the tagged samples are mixed and sequenced, and the sequences from each sample then are identified by their respective sample-specific sequence tags.

FIG. 1 provides a general depiction of various aspects and embodiments of the invention in this regard, and the figure is discussed by way of illustration below with reference to sequencing DNA from different samples. A plurality of samples ($S_1$, $S_2$, through $S_j$) is shown topmost in the Figure.

Each sample is comprised of a plurality of polynucleotides ($P_{1-1}$ to $P_{1-n1}$ in $S_1$; $P_{2-1}$ to $P_{2-n2}$ in $S_2$; through $P_{j-1}$ to $P_{j-nj}$). The polynucleotides in each sample are labeled separately with a tag polynucleotide sequence, all the polynucleotides in a given sample being tagged (in this illustration) with a single tag sequence, designated in the figure as $T_1$ for $S_1$, $T_2$ for $S_2$, through $T_j$ for $S_j$. The individual tagged polynucleotides are denoted accordingly. The tagged polynucleotides in each sample are designated collectively, for each sample, $T_1S_1$, $T_2S_2$ through $T_jS_j$. The tagged polynucleotides from the samples are mixed together to form a mixture, designated M. The mixture is sequenced typically by a parallel sequencing method. The tag sequences are identified in the data thus obtained. The sequences are grouped by tag. The sequences from the individual samples are thereby identified.

In embodiments tags are 3 to 30, 4 to 25, 4 to 20 base long sequences. In embodiments the tags are 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 nucleotides long or any combination thereof.

In embodiments there are 1-6, 6-12, 10-15, 10-20, 15-25, 20-40, 25-50, 25-75, 50-100, 50-150, 100-200, 100-250, 50-250, 100-500, 500-1,000, 100-1,000, 500-5,000, 100-10,000, 1,000-25,000, 500-50,000, 100-100,000, 1-1,000,000 or more samples, tagged, respectively, with 1-6, 6-12, 10-15, 10-20, 15-25, 20-40, 25-50, 25-75, 50-100, 50-150, 100-200, 100-250, 50-250, 100-500, 500-1,000, 100-1,000, 500 -5,000, 100-10,000, 1,000-25,000, 500-50,000, 100-100,000, 1 1,000,000 or more different tags.

In embodiments the sequences are determined without the use of gel electrophoresis. In embodiments the sequences are determined without the use of transfer of sequences from a gel onto a membrane or a filter for hybridization. In embodiments, sequences are determined by a parallel sequencing method. In embodiments the sequences are determined by pyrosequencing, sequencing by synthesis, hybridization sequencing, subtractive sequencing, pore sequencing or direct read sequencing.

In embodiments the tags are incorporated into polynucleotides in samples for sequencing by a step of ligation and/or by a step of amplification.

In embodiments the tags are comprised in primers for amplification.

In embodiments the tags are comprised in primers for PCR amplification, transcription amplification, rolling circle amplification, or amplification by Qβ replicase.

In embodiments the tags are comprised in emulsion PCR adapters and primers for amplification.

In embodiments the tags are incorporated by a step of cloning into a vector.

In embodiments the samples are microbial community samples. In embodiments the samples are clinical samples. In embodiments the samples are environmental samples. In embodiments the samples are samples for SNP analysis. In embodiments the samples are samples for genotyping. In embodiments the sequences are determined in one or more picotiter plates.

In embodiments the samples are fragmented genomic DNAs. In embodiments the samples are fragmented Bacterial genomic DNA, Archae genomic DNA, Fungal genomic DNA, Eukaryotic genomic DNA, chloroplast DNA, and/or mitochondrial DNA. In embodiments the samples are cDNAs. In embodiments the samples are Eukaryotic cDNA, Bacterial cDNA, Archae cDNA, and/or Fungal cDNA. In embodiments the tags are incorporated by a step of ligation and/or by a step of amplification.

In embodiments the samples are for any one or more of detecting, monitoring, profiling, prognosticating, and/or diagnosing a disorder, disease, or the like.

In embodiments the samples are for analyzing the composition, diversity, stability, dynamics, and/or changes in agricultural, food, biosecurity, veterinary, clinical, ecological, zoological, oceanological, and/or any other sample comprising one or more polynucleotides.

In embodiments the sequences are determined in wells of a titer plate. In embodiments the sequences are determined in one or more picotiter plates having a mask. In embodiments the sequences are determined in one more picotiter plates having a mask, wherein the mask defines 2, 4, 8, 16, 32, 64 or more compartments.

By way of illustration to a 454 picotiter plate, in embodiments there are about 120,000 templates/plate and the read length averages about 250 bases per template. In embodiments relating thereto there are 10 tags of 4 bases per 1/16 plate, 160 tags total, an average of about 750 templates per tag (and per sample), and about 187,500 bases sequenced per tag (and per sample).

In embodiments there are about 260,000 templates/plate and the read length averages about 250 bases per template. In embodiments relating thereto, there are 12 tags of 4 bases per 1/8 plate, 96 samples total, an average of about 2,708 templates per tag (and per sample) and about 677,083 bases of sequence per tag (and per sample).

In embodiments there are about 400,000 templates/plate and the read length averages about 250 bases per template. In embodiments relating thereto, there are 96 tags of 6 bases for 96 samples per plate, about 4,166 templates per tag (and per sample) and about 1,041,666 bases of sequence per tag (and per sample).

In embodiments the tags are 10 base long sequences, there are 192 different tags, and the samples are analyzed in microtiter plate format.

In embodiments the invention provides algorithms for deconvolving, from a mixture of sequences from two or more samples, the sequences of the samples in the mixture by identifying sample-specific tags in the sequences, grouping the sequences by the tags thus identified, thereby grouping together the sequence from each of said samples, apart from one another.

In embodiments the invention provides algorithms for deconvolving, from a mixture of sequences from two or more samples, the sequences of the samples in the mixture by identifying sample-specific tags in sequences, as follows:
1. Read all sequence reads into an array;
2. Search the beginning of each sequence read and identify the tag;
3. Build an associative array linking tag with sequence read;
4. Sort the keys for the associate array;
5. Associate each key with the corresponding sample;
6. Pool all sequence reads for each sample;
7. Analyze each sample separately.
8. Normalize the abundance of each component within each samples with respect to the total reads within that sample.

In embodiments the algorithm can be implemented in any programming language. In embodiments the algorithm is implemented in C, C++, JAVA, Fortran, or Basic. In embodiments the algorithm is implemented as a PERL script.

In embodiments the invention provides kits for multiplex sequencing as described herein, comprising a set of primers and/or adapters, wherein each primer and/or adapter in said set comprises a tag sequence, a primer sequence and/or an emulsion PCR adapter. In embodiments the primers and/or adapters further comprise a moiety for immobilization. In embodiments the primers and/or adapters comprise biotin. In embodiments the primers and/or adapters in the set comprise all tag sequences defined by 2, 3, 4, 5, 6, 7, or 8 base polynucleotide sequences, wherein said primers and/or adapters comprising different tag sequences are disposed in containers separate from one another. In embodiments there are 1-5, 3-10, 5-15, 10-25, 20-50, 25-75, 50-100, 50-150, 100-200, 150-500, 250-750, 100-1000, or more different tag sequences disposed separately from one another, so as to be useful for uniquely tagging said number of different samples. In embodiments the primers and/or adapters are suitable for use as 454 Life Sciences amplification adapters and/or primers. In embodiments the primers and/or adapters further comprise any one or more of a primer sequence for any one or more of a 16S rRNA sequence, an 18S rRNA sequence, an ITS sequence, a mitochondrial sequence, a microsatellite sequence, a metabolic enzyme sequence, a genetic disease sequence, and/or any other sequence for amplification or analysis.

EXAMPLES

The present invention is additionally described by way of the following illustrative, non-limiting examples.

Example 1

Sequencing Using the 454 Pyrosequencing System

454 Life Sciences, a subsidiary of Roche Diagnostics, provides a device for pyrosequencing approximately 100,000,000 bases of about 400,000 different templates in a single run on a single picotiter plate. The company also provides masks that allows for the processing 2, 4, 8, or 16 different samples on one plate. At maximum capacity using the masked plate, the system provides about 1 million bases of sequence data on about 4,000 templates for each of 16 samples.

The general process of sequencing using the 454 system is generally as follows: isolate DNA; optionally fragment the DNA; optionally render the DNA double stranded; ligate the DNA to adaptors; separate the strands of the dsDNA, bind the ssDNA to beads under conditions that result in a preponderance of beads that have either no DNA molecule bound to them or a single molecule of DNA bound to them; capture the beads in individual droplets of an emulsion of a PCR reaction mix in oil; carry out a PCR reaction on the emulsion-encapsulated bead-DNAs (whereby amplification products are captured on the beads); distribute the amplification products into picoliter wells so that there is either no bead in a well or one bead; and carry out pyrosequencing on all the beads in all the wells in parallel.

Example 2

Multiplex Pyrosequencing Using 96 Tagged Adapter-PCR Primers

454 Life Sciences, a subsidiary of Roche Diagnostics, provides a device for pyrosequencing approximately 100,000,000 bases of sequence for about 400,000 different templates in a single run on a single picotiter plate. At maximum capacity using the plate, the system provides about 10 million bases of sequence data for each of about 4,000 templates for each of 96 multitagged samples. In this example the 96 tags are 6 bases in length and are used along with 6 bases of the forward or reverse primer to identify the reads that belong with each of the 96 individual samples (see FIG. 2).

Example 3

Multtag Pyrosequence Analysis of Microbial Community Samples

Various aspects and embodiments of the invention herein described are illustrated by way of the following general example relating to "ecogenomic" analysis of microbial diversity in biological samples.

The ability to quantify the number and kinds of microorganisms within a community is fundamental to the understanding of the structure and function of an ecosystem, as discussed in, for instance, Pace 1997 and Theron and Cloete 2000. Traditionally, the analysis of microbial communities has been conducted using microbiological techniques, but these techniques are limited. For instance they are not useful for the many organisms that cannot be cultivated (Ritchie, Schutter et al. 2000; Spring, Schulze et al. 2000). Even for those organisms that can be cultured, these techniques provide little information with which to identify individual microbes or characterize their physiological traits. (Morris, Bardin et al. 2002).

Recent advances in molecular techniques have overcome some of these disadvantages, and have enabled the identification of many more taxa in microbial communities than traditional microbial techniques. These advances have provided considerable insight into the expression of key functions in species in microbial communities. (Pace 1997; Suzuki 1998; Amann 2000; Frischer, Danforth et al. 2000; Ritchie, Schutter et al. 2000; Spring, Schulze et al. 2000). Among these molecular techniques are Denaturing Gradient Gel Electrophoresis (DGGE), Temperature Gradient Gel Electrophoresis (TGGE), Temporal Temperature Gradient Gel Electrophoresis (TTGE), Terminal-Restriction Fragment Length Polymorphism (T-RFLP), Single Strand Conformation Polymorphism (SSCP), and Length Heterogeneity PCR (LH-PCR) (Frischer, Danforth et al. 2000; Theron and Cloete 2000; Mills, Fitzgerald et al. 2003; Seviour, Mino et al. 2003; Klaper and Thomas 2004).

Among these, LH-PCR is probably the best technique for fingerprinting. It is inexpensive, fast, and can be used routinely to screen several hundred samples a day. It is useful as a routine survey tool that can be used to monitor the dynamics of natural soil microbial communities, and to quickly identify samples of interest by PCO analysis. LH-PCR has been used to extensively assess natural variation in bacterial communities by profiling the amplified variable regions of 16S rRNA genes in mixed microbial population samples, using PAGE. (See Mills 2000; Litchfield and Gillevet 2002; Lydell, Dowell et al. 2004). The LH-PCR products of the individual species in the population give rise to distinct bands in the gels. The "peak area" of each band is proportional to the abundance of the species in the community. LH-PCR of 16S rRNA variable regions has been used quite successfully to estimate species diversity in bacterioplankton communities, in particular. (See Suzuki, Rappe et al. 1998; Ritchie, Schutter et al. 2000).

Community functionality cannot be determined directly from 16S rRNA clone data, however, it must be inferred from the data by phylogenetic analysis. Furthermore, LH-PCR and other fingerprinting technologies, while powerful tools for monitoring population dynamics, cannot identify individual species in a community. For this, fingerprinting investigations must be followed up by library construction, cloning, sequencing, and phylogenetic analysis. (Fitzgerald 1999; McCraig 1999; Spring, Schulze et al. 2000; Theron and Cloete 2000; Litchfield and Gillevet 2002; Bowman and McCuaig 2003; Kang and Mills 2004; Eckburg, Bik et al. 2005). Identifying species of a fingerprinting study, thus, is a considerable undertaking that is inconvenient, time-consuming, expensive and subject to technical limitations.

Grouping samples can, to some extent, reduce the cost, time, and expense of such analyses. For instance, PCO analysis of LH-PCR data can be used to group samples with similar profiles for batch cloning and sequencing. Combining the samples this way reduces the time, expense, and work involved in analyzing the samples. Sequencing of at least 300 random clones is required to identify the bacterial components of the pooled sample down to 1% of the total bacterial populations in typical samples. This level of resolution is similar to that of ALH fingerprinting. Originally a novel approach, pooling similar samples prior to cloning and sequencing has proven to be robust and effective.

In classic community studies in the literature (Eckburg, Bik et al. 2005), environmental samples are assayed independently. Then the clone sequence data from specific classes/groups are statistically analyzed usually using some sort of averaging metric. Analyses of this type can be extremely costly, especially if the clone libraries are exhaustively analyzed, something that typically involves sequencing thousands of clones. Moreover, for the "averaging" process to be valid, as required for comparing the mixed populations, the samples must be pooled in equal proportions. While simple in principle, in reality, it is difficult to accomplish and, even if accomplished, impossible to verify. A new technique, based on pyrosequencing, offers advantages that overcome a variety of these drawbacks of the fingerprinting technologies mentioned above. The method is implemented on an instrument sold by 454 Life Sciences, Inc., a subsidiary of Curagen Sciences, Inc., using reagents provided by the same company. In addition, 454 Life Sciences provides a custom service for pyrosequencing.

In this technology, individual DNA molecules are amplified on beads by PCR in individual droplets in an oil-in-water emulsion. Beads then are deposited individually in wells of a picotiter plate. The sequences of all the DNAs in the wells are determined in parallel by pyrosequencing. (See Venter, Levy et al. 2003; Margulies, Egholm et al. 2005; Poinar, Schwarz et al. 2006). In a typical run, there are about 200,000 templates per plate, an average read length of about 100 bases from each template, and a single-plate run generates about 20 million bases of sequence in a single four hour run.

Although the technology greatly increases throughput over previous methods, it is expensive. In particular, the cost per plate is too high for it to be economically practical to carry out many analyses. To decrease cost, masks can be used that divide a plate into 16 independent sample zones, so that one plate can be used to process 16 different samples, either at the same time or independently. Each 1/16 zone provides about 1,000,000 bases of sequence data from about 10,000 different templates. While this reduces the cost per sample, the expenses associated with using this technology remain undesirably high.

Various aspects and embodiments of the present invention can be used to further reduce the cost per sample of this technology (as well as other techniques, as described elsewhere herein). The use of multitagging techniques (referred to as, among other things, "Multitag Process") to the genomic analysis of bacterial populations in according with certain aspects and embodiments of the invention, notably high coverage sequencing of bacterial communities, is referred to herein as "Multitag Ecogenomics" and also as "Multitag Ecogenomic Analysis."

(Several publications use the term "Multiplex Pyrosequencing" (Pourmand, Elahi et al. 2002) to refer to generating a composite signal from multiple targets that is read as a signature for a specific sample. The term is not used to refer to tag-based multiplexing in which sequences from different samples in a mixture are determined and then deconvolved from the mixed sequencing data using sample-specific tags incorporated during amplification reactions.)

As described below the Multitag Process in a relatively simple series of steps accomplishes everything that otherwise would require not only community fingerprinting analysis, but also all of the cloning and sequencing processes previously required for high coverage Ecogenomic Analysis using conventional techniques.

By way of illustration, the following example describes the use of Multitag Ecogenomic Analysis of variable regions of common genes using tagged universal primers for high coverage analysis of several microbial community samples all at the same time. The analysis is carried out much as described in general above, and further elaborated on in detail below.

Briefly, short tags are added to the 5' ends of the forward and reverse PCR primers normally used for community analysis. These tags can be placed between the Emulsion PCR adapters and the PCT primers (see FIG. 2). A different tag is attached to the primers for each of the samples to be combined. For instance primers that span a variable region of 16S rRNA genes may be used for analysis of bacterial and archael communities. 16S rRNA-specific primers with 4 base tags are set out in the Table 1 below. Likewise primers that span a variable region of an ITS gene may be used for analysis of fungal communities. It will be appreciated that the choice of these specific primers is not exclusive, and that a wide variety of other primers suitable to other target regions for amplification may be employed in much the same manner as descried herein for the 16S and ITS genes. Thus, any gene of interest can be used that provides conserved primer sites across a community, and sufficient variation in the region between the primers for the desired resolution of individual species. Thus, for example, genes specific to functional pathways such as anaerobic methane oxidation, or sulphur reduction can serve as targets for the amplification reaction, as well as 16S rRNA sequences.

TABLE 1

Forward Shared Sequences (SEQ ID NOS: 193-203) respectively in order of appearance, and Reverse Shared Sequences (SEQ ID NOS: 204-214) resepectively in order of appearance.

| Name | Tag | |
|------|-----|---|
| | | Forward Shared Sequence |
| | | AGCTAGAG TTT GATCMTGGCTCAG |
| L27FA | AGCT | AGCTAGAGTTTGATCMTGGCTCAG |
| L27FB | AGTC | AGTCAGAGTTTGATCMTGGCTCAG |
| L27FC | GATC | GATCAGAGTTTGATCMTGGCTCAG |

TABLE 1-continued

Forward Shared Sequences (SEQ ID NOS: 193-203) respectively in order of appearance, and Reverse Shared Sequences (SEQ ID NOS: 204-214) resepectively in order of appearance.

| Name | Tag | |
|---|---|---|
| L27FD | GACT | GACTAGAGTTTGATCMTGGCTCAG |
| L27FE | CTGC | CTGCAGAGTTTGATCMTGGCTCAG |
| L27FF | CTAG | CTAGAGAGTTTGATCMTGGCTCAG |
| L27FG | ATGC | ATGCAGAGTTTGATCMTGGCTCAG |
| L27FH | ATAG | ATAGAGAGTTTGATCMTGGCTCAG |
| L27FM | ATCT | ATCTAGAGTTTGATCMTGGCTCAG |
| L27FO | ATAT | ATATAGAGTTTGATCMTGGCTCAG |
| | Reverse Shared Sequence | |
| | | *AGCTGCTGCCTCCCGTAGGAGT* |
| 355RA | AGCT | AGCTGCTGCCTCCCGTAGGAGT |
| 355RB | AGTC | AGTCGCTGCCTCCCGTAGGAGT |
| 355RC | GATC | GATCGCTGCCTCCCGTAGGAGT |
| 355RD | GACT | GACTGCTGCCTCCCGTAGGAGT |
| 355RE | CTGC | CTGCGCTGCCTCCCGTAGGAGT |
| 355RF | CTAT | CTATGCTGCCTCCCGTAGGAGT |
| 355RG | ATGC | ATGCGCTGCCTCCCGTAGGAGT |
| 355RH | ATAT | ATATGCTGCCTCCCGTAGGAGT |
| 355RM | ATCT | ATCTGCTGCCTCCCGTAGGAGT |
| 355RO | ATAC | ATACGCTGCCTCCCGTAGGAGT |

Table 1 shows a 16S rRNA-specific primer with a variety of 4 base tag sequences attached. As described herein such primers are useful for amplifying 16S rRNAs in several samples that can then be sequenced together. The 16S rRNA in each sample is amplified using a different tag, but the same 16S primer sequence. The amplified rRNA sequences from the samples are combined and sequenced together. The rRNA sequences from the different samples then are identified and sorted out by their 4 base tag sequence plus the first 4 bases of each primer. It is to be appreciated that the sequences downstream of the shared 16S primer sequence will differ among the samples, as well as the tag sequence.

In each case, the samples are individually amplified. The resulting amplicons comprise the primer sequences including the tags. Since unique tags are used for each sample, the tags in the amplicons from each sample will be different. The amplified DNAs are then pooled and sequenced by pyrosequencing as described above. The sequence data from a run is analyzed, in part, by grouping together all the sequences having the same tag. In this way, the sequences from each sample are demultiplexed from the sequencing data obtained from the mixture.

The working of the invention in this regard is illustrated by the following simulation, carried out using conventionally obtained population data from cold seep samples. The algorithm for sequence analysis uses a PERL script to extract the first 100 bases of sequence. It then analyzes all the 100 bases sequences using a custom RDP PERL script. The script works as follows:

1. Read all sequence reads into an associate array (Hash 1);
2. Extract 100 base subsequences from the beginning of each sequence read;
3. Create an associate array (Hash 2) of the sequences;
4. Perform a Blast search of the RDP database with Hash 1;
5. Perform a Blast search of the RDP database with Hash 2;
6. Compare the identifications for the original sequence (Hash 1) and the subsequence (Hash 2);
7. Compile a list of similar identifications for Hash 1 and Hash 2;
8. Compile a list of different identifications for Hash 1 and Hash 2;
9. Calculate the percentage of similar identifications.

As shown below, there is virtually no difference at the class level in the microbial diversity generated by the sequencing simulation and that derived directly from the 16S rRNA sequences in the data base.

TABLE 2

| RDP Class | First 100mer | 16S rRNA |
|---|---|---|
| ALPHA_SUBDIVISION | 3.6% | 3.6% |
| ANAEROBIC_HALOPHILES | 3.6% | 3.6% |
| *BACILLUS-LACTOBACILLUS-STREPTOCOCCUS* SUBDIVISION | 3.6% | 3.6% |
| *BACTEROIDES*_AND_*CYTOPHAGA* | 7.1% | 7.1% |
| *CHLOROFLEXUS*_SUBDIVISION | 3.6% | 3.6% |
| *CY. AURANTIACA*_GROUP | 7.1% | 7.1% |
| CYANOBACTERIA | 7.1% | 7.1% |
| DELTA_SUBDIVISION | 14.3% | 14.3% |
| ENVIRONMENTAL_CLONE_WCHB1-41 _SUBGROUP | 7.1% | 7.1% |
| *FLX. LITORALIS*_GROUP | 3.6% | 3.6% |
| GAMMA_SUBDIVISION | 10.7% | 10.7% |
| HIGH_G + C_BACTERIA | 7.1% | 7.1% |
| *LEPTOSPIRILLUM* GROUP | 3.6% | 3.6% |
| MYCOPLASMA_AND_RELATIVES | 3.6% | 3.6% |
| *PIRELLULA*_GROUP | 3.6% | 3.6% |
| *SPHINGOBACTERIUM*_GROUP | 3.6% | 3.6% |
| *SPIROCHAETA-TREPONEMA-BORRELIA*_SUBDIVISION | 3.6% | 3.6% |
| *THERMOANAEROBACTER*_AND_RELATIVES | 3.6% | 3.6% |

Example 3

Multitag Pyrosequence Analysis of Dysbiosis in IBD

Inflammatory Bowel Diseases (IBD or IBDs), namely ulcerative colitis (UC) and Crohn's disease (CD), are chronic, lifelong, relapsing illnesses, affecting close to 1 million Americans and costing approximately $2 billion per year to the US healthcare system. IBDs are of unknown cause, have no cure, and are increasing in incidence. The natural course of these diseases is characterized by periods of quiescence (inactive disease) interspersed with flare-ups (active disease). It is now widely accepted that flare-ups of IBD are due to a dysregulated inflammatory reaction to abnormal intestinal microflora dysbiosis), however.

Specific changes in the microflora of IBD patients that might cause these diseases remain unknown. Narrow searches for a single pathogen that causes IBD have been unsuccessful. (See Guarner and Malagelada 2003). Studies of small bacterial groups have yielded ambiguous results. (See Schultz and Sartor 2000). Only recently have studies of large sets of bacterial flora been attempted. (See Eckburg, Bik, et al. 2005). Improving our knowledge about GI tract microflora has the potential to revolutionize IBD treatment. Development of real-time methods to study microfloral changes may lead to diagnostic tools to predict flare-ups, and to targeted, safe treatments for IBD.

The key requirement to understanding dysbiosis in polymicrobial diseases is for a method to interrogate widely the microflora in numerous control and disease samples to identify dynamic trends in species composition associated with health and disease progression. In classic community studies (Eckburg, Bik, et al. 2005) environmental samples are assayed independently and then the clone sequence data from specific classes/groups are statistically analyzed usually using some sort of averaging metric. This can be extremely costly, especially if the clone libraries are exhaustively analyzed (i.e., 10,000 clones per sample).

To improve throughput and reduce cost, Amplicon Length Heterogeneity PCR (ALH-PCR) has been used to study the gut microflora. It offers a rapid way of screening complex microbial communities, allowing for easy fingerprinting of microfloral changes. The LH-PCR fingerprinting is inexpensive and fast, with the ability to screen several hundred samples a day. It can be used as a routine survey tool to monitor the dynamics of natural soil microbial communities or to quickly identify samples of interest using PCO analysis. PCO analysis has been used to group samples with similar profiles, allowing them to be pooled for cloning and sequencing. This greatly reduces the cost of analyzing multiple samples, particularly when the analysis requires sequencing at least 300 random clones to identify bacterial components of the sample down to 1% representation in the total population (which is the resolution limit for ALH fingerprinting). Pooling similar samples before cloning and sequencing has proved to be quite robust. However, equal amounts of the PCR product from each sample must be pooled or the results will be skewed.

Multitag Pyrosequencing is a novel pyrosequencing technology that allows many community samples to be sequenced together at high coverage without the necessity for fingerprinting, cloning, or the purification and separation techniques required by conventional methods for analyzing microbial communities, as described herein above. Multitag sequencing is more efficient, faster, and less costly than other methods.

Figure 2A:
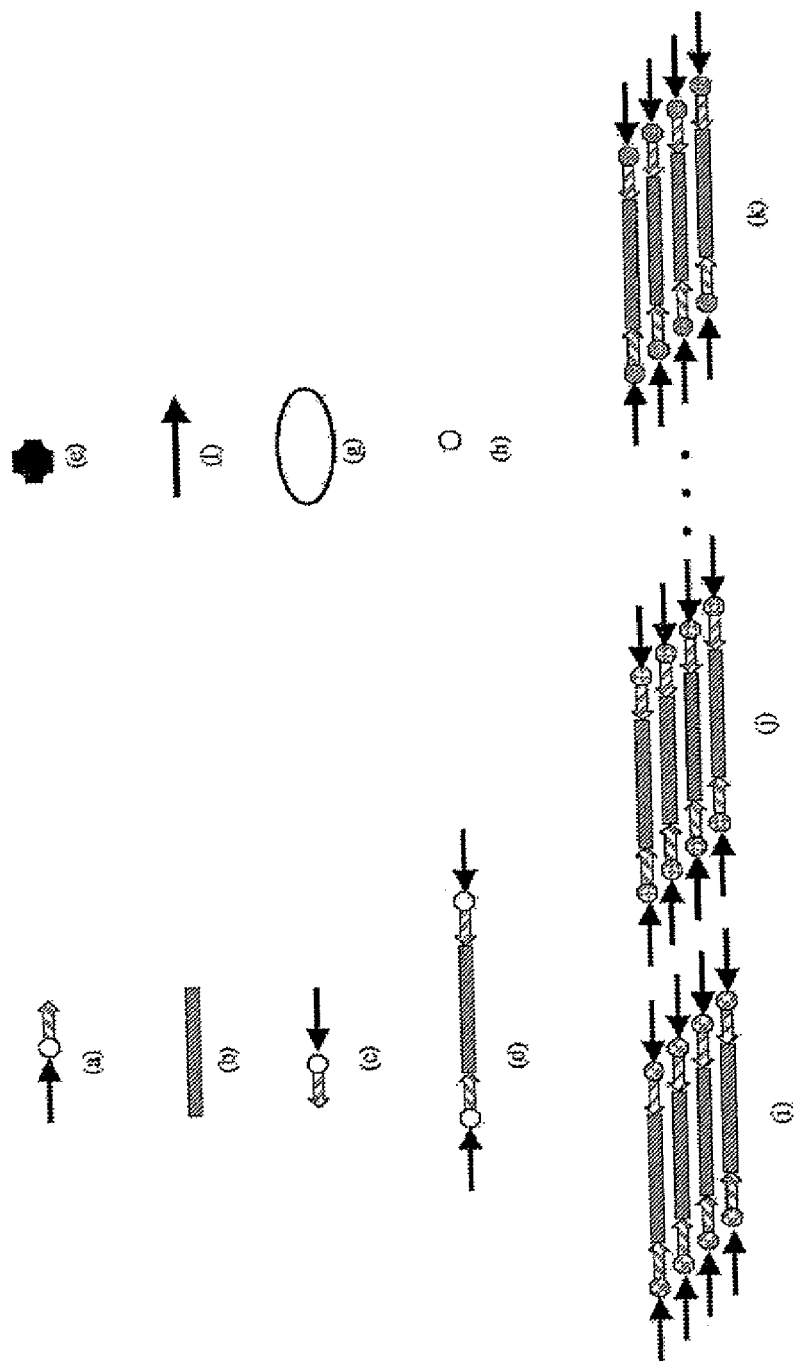
FIG. 2A is a diagram depicting step I in the multitag sequencing of microbial community samples using a tagged 16S forward and reverse primer-linker pairs for PCR amplification. (a) represents the Forward 16S rRNA primer with Tag I and Emulsion PCR Linker, (b) represents the 16S rRNA sequence, (c) represents the Reverse 16S rRNA primer with Tag j and Emulsion PCR Linker, (d) represents the Amplified 16S rRNA sequence with Forward and Reverse Tags ij, (e) represents the Emulsion PCR Bead, (f) represents the pyrosequencing read, (g) represents the well in picoliter plate, (h) represents a Unique tag, (i) represents Amplified Community 1, (j) represents Amplified Community 2, and (k) represents Amplified Community n. Step 1 involves the amplification of the microbial community from each sample using uniquely tagged universal primers-linkers. In step 1, different samples are amplified separately, using 16S rRNA specific adapter-tag-primers with a different tag for each sample.
Figure 2D:
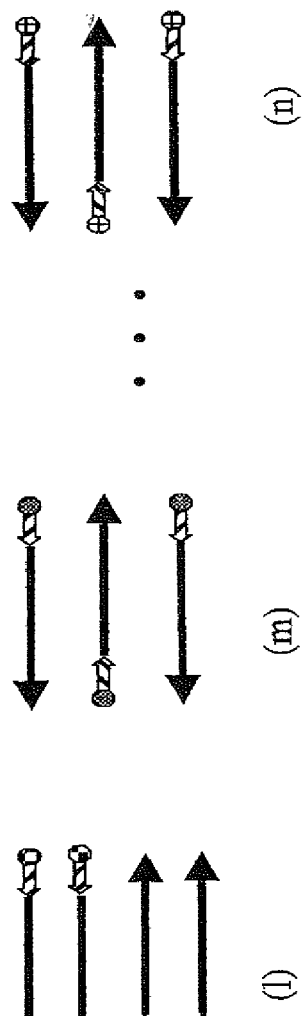
FIG. 2D is a diagram depicting the algorithmic sorting of the Pyrosequencing reads using the individual tag sequence and a portion of the primer sequence. (1) represents the sequence reads from sample 1, (m) represents the sequence reads from sample 2, and (n) represents the sequence reads from sample n.
Figure 2E:
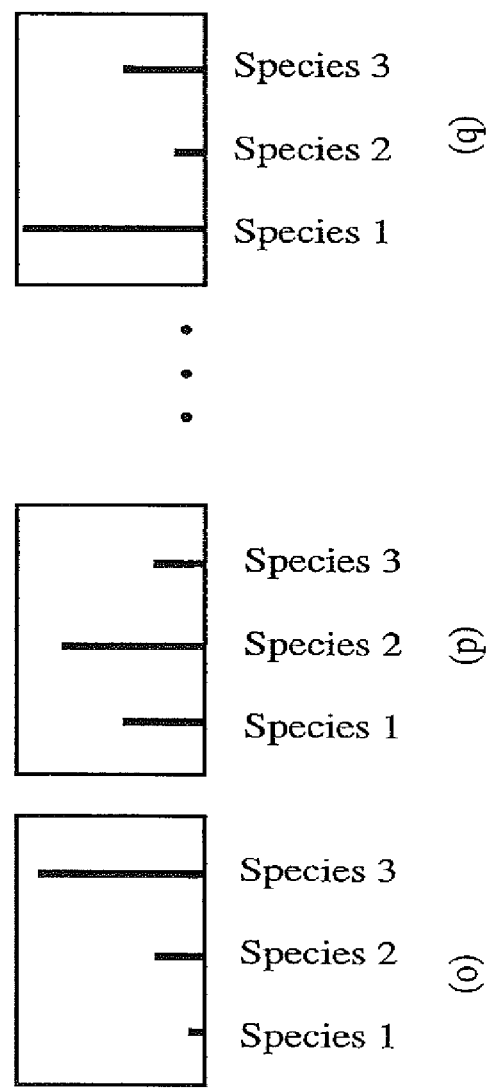
FIG. 2E is a diagram depicting the identification of microbial taxa by comparing the sequence reads for each sample against the 16S rRNA sequence database and then normalize abundance in each taxa with respect to the total reads in that particular sample. (o) represents the normalized species histogram derived the pyrosequencing reads obtained from sample 1, (p) represents the normalized species histogram derived the pyrosequencing reads obtained from sample 2, (q) represents the normalized species histogram derived the pyrosequencing reads obtained from sample n.

By way of illustration, Multitag Pyrosequencing can be carried out using a set of specific tags on the end of standard universal small ribosomal sub-unit ("SSU") rRNA primers (See Table 1). A different set of the tagged primers is used to amplify the SSU rRNA in each different environmental sample (FIG. 2—Step 1). The PCR amplicons from all the samples are pooled. Emulsion PCR is performed and the amplicons arising from each molecule are captured on their respective beads. Following amplification, the beads are distributed into the wells of a picoliter plate (FIG. 2—Step 2). The sequences, including the tagged sequences, of the amplicons on each bead are determined by pyrosequencing (FIG. 2—Step 3). A PERL script or other suitable program is used to sort the sequence information using the tags and primer sequence as a key. Sequences with the same tags are identified thereby with their respective sample. The bacteria species in each sample then are identified by matching the SSU rRNA sequences to entries in the database of the Ribosomal Database Project (either RDP 8.1 or RDP 9.0). The normalized frequency with which a bacteria is thus identified in a given sample is indicative of its relative representation in the microbial community. Histograms based on these frequency determinations can be used for the non-parametric analysis of dysbiotic shifts involved in disease states.

For example, FIG. 3 depicts the results of such an experiment in which six Control, ten Crohns, and eight Ulcerative colitis mucosal samples were analyzed by Multitag Pyrosequencing. Each of the segments in the stacked histogram bars represents the normalized abundance of that specific taxa in a specific sample. In this experiment, identification of the taxa was performed using BLAST analysis of the RDP 8.1 database. It can be seen that some taxa (i.e. *Bacillus fragilis* subgroup and *Rumanococcus gnavus* subgroup) are present in the same abundance in both control and disease states. Other taxa, such as *Clostridium leptum* are more dominant in Ulcerative colitis, while others (i.e. the *Gloeothece gloeocapsa* subgroup) are indicators of dysbiosis in the disease state.

However, the standard 454 Life Science process using a ligation step to link the emulsion PCR adapters to the PCR amplicons and produces numerous artifacts in the quantitation of the abundances of each taxa in the samples. In the results displayed in FIG. 3, we algorithmically removed chimeras, reverse reads and truncated products and filtered the data to remove all taxa that were represented by less than 5% abundance. Only then were we able to see a correlation with disease state and specific microbial taxa.

Example 4

Figure 4A:
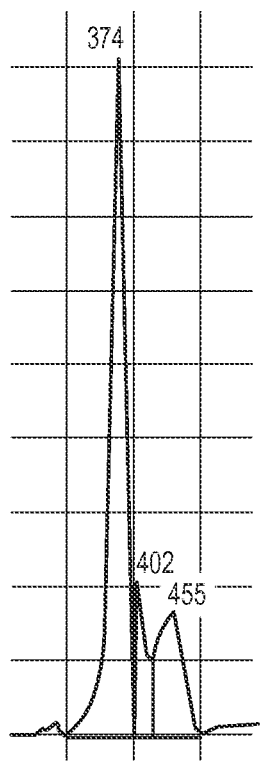
FIGS. 4A and 4B show an example of the distortion of the components of a complex mixture caused by ligating the Emulsion PCR adapters onto PCR amplicons.
Figure 4B:
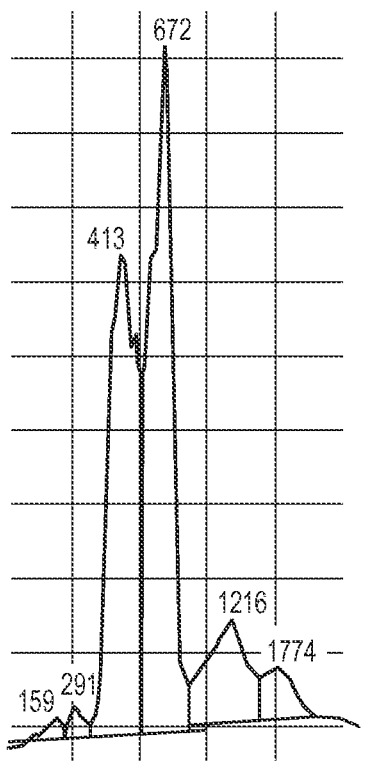

Distortion of the Distribution of Components of a Microbial Community by Directly Ligating Emulsion PCR Adapters onto PCR Amplicons In one experiment we used tagged PCR primers to amplify the components in duplicate microbial community samples, ligated the Emulsion PCR adapters to these samples, and then subjected these samples to separate pyrosequencing runs. The amplicons are routinely run on an Agilent Bioanalyzer system before and after ligation to quantitate the mixture before emulsion PCR. FIG. 4 depicts a sample run on the Bioanalyzer before and after direct ligation and clearly shows that the ligation step has drastically altered the distribution of the amplicons.

Additionally, we compared the normalized abundances of the component taxa identified by the multitag process after direct ligation of the Emulsion PCR adapters. In this experiment, identification of the taxa was performed using a Bayesian analysis of the RDP 9.0 database. We can se in FIG. 5 that abundances of the forward and reverse primers for various taxa are different within a sample and between duplicate samples. In several cases, we are missing entire families in the comparison between duplicates. Table 3 summarizes the differences between the forward primers and the reverse primers of the duplicate samples and it is clearly stochastic with no predictable pattern. We hypothesize that this differential ligation efficiency could be due to a number of factors such as internal structure in the amplicons or biases in the terminal nucleotide of either the adapter or amplicon.

TABLE 3

Duplicate Sample Analysis

| RDP 9.0 FAMILY | FORWARD PRIMERS RATIOS | REVERSE PRIMER RATIOS |
|---|---|---|
| Acidaminococcaceae | 544.6% | 195.0% |
| Actinomycetales | 144.0% | 116.5% |
| Bacteroidaceae | 119.9% | 124.5% |
| Clostridiaceae | 97.5% | 99.4% |
| Comamonadaceae | 198.0% | |
| Coriobacteriales | 181.5% | 141.5% |
| Enterobacteriaceae | 4.2% | |
| Eubacteriaceae | 88.0% | 87.5% |
| Flavobacteriaceae | 34.9% | |
| Incertae sedis 9 | 106.4% | 143.0% |
| Lachnospiraceae | 176.8% | 113.1% |
| Peptococcaceae | | 91.0% |
| Peptostreptococcaceae | 94.7% | 115.4% |
| Porphyromonadaceae | 99.0% | 97.3% |
| Prevotellaceae | 264.0% | 88.1% |
| Rikenellaceae | 212.2% | 106.1% |
| Streptococcaceae | 74.3% | 60.7% |

LITERATURE CITED

Each of the following publications is incorporated herein by reference in its entirety, particularly as to the above-referenced subject matter, especially relating to methods that can be employed in carrying out multitag sequencing and/or relating to uses thereof.

Amann, R. (2000). "Who is out there? Microbial Aspects of Biodiversity." System. Appl. Microbiol. 23: 1-8.

Bowman, J. P. and R. D. McCuaig (2003). "Biodiversity, Community Structural Shifts, and Biogeography of Prokaryotes within Antarctic Continental Shelf Sediment." Appl. Environ. Microbiol. 69(5): 2463-2483.

Eckburg, P. B., E. M. Bik, et al. (2005). "Diversity of the human intestinal microbial flora." Science 308: 1635-1638.

Fitzgerald, K. M. (1999). Microbial Community Dynamics During the Bench-Scale Bioremediation of Petroleum-Contaminated Soil. Department of Biology. Fairfax, Va., George Mason University: 73.

Frischer, A. E., J. M. Danforth, et al. (2000). "Whole-cell versus total RNA extraction for analysis of microbial community structure with 16S rRNA-targeted oligonucleotide probes in salt marsh sediments." Appl. Environ. Microbiol. 66(7): 3037-3043.

Guarner, F., and J. R. Malagelada. (2003). "Gut flora in health and disease." Lancet 361: 512-9.

Kang, S. and A. L. Mills (2004). "Soil Bacterial Community Changes Following Disturbance of the Overlying Plant Community." Soil Science 169: 55-65.

Klaper, R. and M. Thomas (2004). "At the crossroads of genomics and ecology: the promise of a canary on a chip." BioScience 54: 403-412.

Litchfield, C. D. and P. M. Gillevet (2002). "Microbial diversity and complexity in hypersaline environments: A preliminary assessment." Journal of Industrial Microbiology & Biotechnology 28(1): 48-55.

Lydell, C., L. Dowell, et al. (2004). "A population survey of members of the phylum Bacteroidetes isolated from salt marsh sediments along the east coast of the United States." Microbial ecology 48(2): 263-73.

Margulies, M., M. Egholm, et al. (2005). "Genome sequencing in microfabricated high-density picolitre reactors." Nature, 2005 September 15, 437(7057):376-80. Epub: 2005 Jul. 31.

McCraig, A. E., L. Glover, J. I. Prosser (1999). "Molecular analysis of bacterial community structure and diversity in unimproved and improved upland grass pastures." Appl. Environ. Microbiol. 65: 1721-1730.

Mills, D. (2000). Molecular Monitoring of Microbial Populations during Bioremediation of Contaminated Soils. Environmental Sciences and Public Policy/Biology. Fairfax, Va., George Mason University: 217.

Mills, D. K., K. Fitzgerald, et al. (2003). "A Comparison of DNA Profiling Techniques for Monitoring Nutrient Impact on Microbial Community Composition during Bioremediation of Petroleum Contaminated Soils." J. Microbiol. Method 54: 57-74.

Morris, C. E., M. Bardin, et al. (2002). "Microbial biodiversity: approaches to experimental design and hypothesis testing in primary scientific literature from 1975 to 1999." Microbiology and Molecular Biology Reviews 66: 592-616.

Pace, N. R. (1997). "A Molecular View of Microbial Diversity and the Biosphere." Science 276: 734-739.

Poinar, H. N., C. Schwarz, et al. (2006). "Metagenomics to paleogenomics: large-scale sequencing of mammoth DNA." Science, 2006 January 20, 311(5759):392-4. Epub: 2005 Dec. 20.

Pourmand, N., E. Elahi, et al. (2002). "Multiplex Pyrosequencing." Nucleic acids research 30(7): 31.

Ritchie, N. J., M. E. Schutter, et al. (2000). "Use of Length Heterogeneity PCR and Fatty Acid Methyl Ester Profiles to Characterize Microbial Communities in Soil." Applied and Environmental Microbiology 66(4): 1668-1675.

Schultz, M., and R. B. Sator. (2000). "Probiotics and inflammatory bowel disease." Am. J. of Gastroenterology 2000 January 95 (1 Suppl): S19-21.

Seviour, R. J., T. Mino, et al. (2003). "The microbiology of biological phosphorus removal in activated sludge systems." FEMS Microbiology Reviews 27: 99-127.

Spring, S., R. Schulze, et al. (2000). "Identification and characterization of ecologically significant prokaryotes in the sediment of freshwater lakes: molecular and cultivation studies." FEMS Microbiology Reviews 24: 573-590.

Suzuki, M., M. S. Rappe, et al. (1998). "Kinetic bias in estimates of coastal picoplankton community structure obtained by measurements of small-subunit rRNA gene PCR amplicon length heterogeneity." Applied and Environmental Microbiology [Appl. Environ. Microbiol.]. 64(11): 4522-4529.

Suzuki, M. T. (1998). The Effect of Protistan Bacterivory on Bacterioplankton Community Structure: Dissertation Abstracts International Part B Science and Engineering [Diss. Abst. Int. Pt. B—Sci. & Eng.]. Vol. 59, no. 2, [np]. August 1998.

Theron, J. and T. E. Cloete (2000). "Molecular techniques for determining microbial diversity and community structure in natural environment." Critical Reviews in Microbiology 26: 37-57.

Venter, J. C., S. Levy, et al. (2003). "Massive parallelism, randomness and genomic advances." Nature genetics, 2003 March, 33 Suppl: 219-27.

What is claimed is:

1. A method for determining microbial community profiles across at least five biological samples, comprising:
   amplifying and tagging a 16S rRNA or 18S rRNA variable region by PCR for each of said samples with an amplification primer pair comprising: a sequencing adaptor, a tag sequence to identify the sample and which is different between the forward and reverse primers of each primer pair, and a probe sequence that is the same for each primer pair;
   combining the amplified polynucleotides and sequencing the polynucleotide pool using a sequencing-by-synthesis sequencer; and
   assigning the nucleotide sequences to the originating samples by the nucleotide sequence of the tags and aligning the nucleotide sequences or subsequences thereof to microbial rRNA reference sequences, thereby
   determining microbial community profiles across the samples.

2. The method of claim 1, wherein the biological samples are clinical samples.

3. The method of claim 2, wherein the clinical samples are derived from patients suspected of having Inflammatory Bowel Disease.

4. The method of claim 3, wherein the Inflammatory Bowel Disease is ulcerative colitis or Crohn's disease.

5. The method of claim 1, wherein the biological samples are environmental samples derived from soil or water.

6. The method of claim 1, wherein the plurality of biological samples is at least 100 samples.

7. The method of claim 1, wherein the 16S rRNA or 18S rRNA variable region varies between microbial species.

8. The method of claim 1, wherein the tag sequence is from 4 to 36 nucleotides in length.

9. The method of claim 8, wherein the tag sequence is 5, 6, 7, 8, 9, 10, 11, or 12 nucleotides in length.

10. The method of claim 1, wherein the tag sequence does not contain any homodinucleotide sequences.

11. The method of claim 1, wherein the tag sequence is not the complementary sequence to any other tag sequence.

12. The method of claim 11, wherein the tag sequence is different by at least two nucleotides across the samples.

13. The method of claim 1, wherein the probe sequence hybridizes to a target sequence that is 3' to the 16S rRNA or 18S rRNA variable region.

14. The method of claim 1, wherein the sequencing is pyrosequencing.

15. A method for determining microbial community profiles across at least five biological samples, comprising:
    amplifying and tagging a 16S rRNA or 18S rRNA variable region by linear amplification for each of said samples with an amplification primer, comprising: a sequencing adaptor, a tag sequence to identify the sample, and a probe sequence that is the same for each primer;
    combining the amplified polynucleotides and sequencing the polynucleotide pool using a sequencing-by-synthesis sequencer;
    assigning the nucleotide sequences to the originating samples by the nucleotide sequence of the tags and aligning the nucleotide sequences or subsequences thereof to microbial rRNA reference sequences, thereby determining microbial community profiles across the samples.

16. The method of claim 15, wherein the biological samples are clinical samples.

17. The method of claim 15, wherein the clinical samples are derived from patients suspected of having Inflammatory Bowel Disease.

18. The method of claim 17, wherein the Inflammatory Bowel Disease is ulcerative colitis or Crohn's disease.

19. The method of claim 15, wherein the biological samples are environmental samples derived from soil or water.

20. The method of claim 15, wherein the plurality of biological samples is at least 100 samples.

21. The method of claim 15, wherein the 16S rRNA or 18S rRNA, variable region varies between microbial species.

22. The method of claim 15, wherein the tag sequence is from 4 to 36 nucleotides in length.

23. The method of claim 22, wherein the tag sequence is 5, 6, 7, 8, 9, 10, 11, or 12 nucleotides in length.

24. The method of claim 15, wherein the tag sequence does not contain any homodinucleotide sequences.

25. The method of claim 15, wherein the tag sequence is not the complementary sequence to any other tag sequence.

26. The method of claim 15, wherein the tag sequence is different by at least two nucleotides across the samples.

27. The method of claim 15, wherein the probe sequence hybridizes to a target sequence that is 3' to the 16S rRNA or 18S rRNA variable region.

28. The method of claim 15, wherein the sequencing is pyrosequencing.

29. The method of claim 1, wherein the average sequencing read length is about 250 nucleotides.

\* \* \* \* \*

SEQUENCE LISTING

<160> NUMBER OF SEQ ID NOS: 214

<210> SEQ ID NO 1
<211> LENGTH: 45
<212> TYPE: DNA
<213> ORGANISM: Artificial Sequence
<220> FEATURE:
<223> OTHER INFORMATION: Synthetic primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 1
gcctccctcg cgccatcaga gacgtagagt ttgatcmtgg ctcag          45

<210> SEQ ID NO 2
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 2
gcctccctcg cgccatcaga gactcagagt ttgatcmtgg ctcag          45

<210> SEQ ID NO 3
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 3
gcctccctcg cgccatcaga gagtcagagt ttgatcmtgg ctcag          45

<210> SEQ ID NO 4
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 4
gcctccctcg cgccatcaga gatgtagagt ttgatcmtgg ctcag          45

<210> SEQ ID NO 5
<211> LENGTH: 45
<212> TYPE: DNA
<213> ORGANISM: Artificial Sequence
<220> FEATURE:

<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 5
gcctccctcg cgccatcaga gcagtagagt ttgatcmtgg ctcag            45

<210> SEQ ID NO 6
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 6
gcctccctcg cgccatcaga gcatcagagt ttgatcmtgg ctcag            45

<210> SEQ ID NO 7
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 7
gcctccctcg cgccatcaga gcgtcagagt ttgatcmtgg ctcag            45

<210> SEQ ID NO 8
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 8
gcctccctcg cgccatcaga gctgtagagt ttgatcmtgg ctcag            45

<210> SEQ ID NO 9
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 9
gcctccctcg cgccatcaga gtagtagagt ttgatcmtgg ctcag    45

<210> SEQ ID NO 10
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 10
gcctccctcg cgccatcaga gtatcagagt ttgatcmtgg ctcag    45

<210> SEQ ID NO 11
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 11
gcctccctcg cgccatcaga gtcgtagagt ttgatcmtgg ctcag    45

<210> SEQ ID NO 12
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 12
gcctccctcg cgccatcaga gtctcagagt ttgatcmtgg ctcag    45

<210> SEQ ID NO 13
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 13
gcctccctcg cgccatcaga gtgtcagagt ttgatcmtgg ctcag    45

<210> SEQ ID NO 14

```
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 14
gcctccctcg cgccatcaga tacgtagagt ttgatcmtgg ctcag            45

<210> SEQ ID NO 15
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 15
gcctccctcg cgccatcaga tactcagagt ttgatcmtgg ctcag            45

<210> SEQ ID NO 16
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 16
gcctccctcg cgccatcaga tagtcagagt ttgatcmtgg ctcag            45

<210> SEQ ID NO 17
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 17
gcctccctcg cgccatcaga tatgtagagt ttgatcmtgg ctcag            45

<210> SEQ ID NO 18
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
```

```
<221> NAME/KEY: source
<222> LOCATION: (1)..(45)
<223> OTHER INFORMATION: /note="Description of Artificial Sequence:
      Synthetic primer"

<400> SEQUENCE: 18
gcctccctcg cgccatcaga tcagtagagt ttgatcmtgg ctcag                45

<210> SEQ ID NO 19
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 19
gcctccctcg cgccatcaga tcatcagagt ttgatcmtgg ctcag                45

<210> SEQ ID NO 20
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 20
gcctccctcg cgccatcaga tcgtcagagt ttgatcmtgg ctcag                45

<210> SEQ ID NO 21
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 21
gcctccctcg cgccatcaga tctgtagagt ttgatcmtgg ctcag                45

<210> SEQ ID NO 22
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 22
```

```
gcctccctcg cgccatcaga tgagtagagt ttgatcmtgg ctcag          45
```

<210> SEQ ID NO 23
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 23

```
gcctccctcg cgccatcaga tgatcagagt ttgatcmtgg ctcag          45
```

<210> SEQ ID NO 24
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 24

```
gcctccctcg cgccatcaga tgcgtagagt ttgatcmtgg ctcag          45
```

<210> SEQ ID NO 25
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 25

```
gcctccctcg cgccatcaga tgctcagagt ttgatcmtgg ctcag          45
```

<210> SEQ ID NO 26
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 26

```
gcctccctcg cgccatcaga tgtgtagagt ttgatcmtgg ctcag          45
```

<210> SEQ ID NO 27
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 27
gcctccctcg cgccatcagc acagtagagt ttgatcmtgg ctcag          45

<210> SEQ ID NO 28
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 28
gcctccctcg cgccatcagc acatcagagt ttgatcmtgg ctcag          45

<210> SEQ ID NO 29
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 29
gcctccctcg cgccatcagc acgtcagagt ttgatcmtgg ctcag          45

<210> SEQ ID NO 30
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 30
gcctccctcg cgccatcagc actgtagagt ttgatcmtgg ctcag          45

<210> SEQ ID NO 31
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:

Synthetic primer"

<400> SEQUENCE: 31
gcctccctcg cgccatcagc agagtagagt ttgatcmtgg ctcag          45

<210> SEQ ID NO 32
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 32
gcctccctcg cgccatcagc agatcagagt ttgatcmtgg ctcag          45

<210> SEQ ID NO 33
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 33
gcctccctcg cgccatcagc agcgtagagt ttgatcmtgg ctcag          45

<210> SEQ ID NO 34
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 34
gcctccctcg cgccatcagc agctcagagt ttgatcmtgg ctcag          45

<210> SEQ ID NO 35
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 35
gcctccctcg cgccatcagc agtgtagagt ttgatcmtgg ctcag          45

```
<210> SEQ ID NO 36
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 36
gcctccctcg cgccatcagc atagtagagt ttgatcmtgg ctcag              45

<210> SEQ ID NO 37
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 37
gcctccctcg cgccatcagc atatcagagt ttgatcmtgg ctcag              45

<210> SEQ ID NO 38
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 38
gcctccctcg cgccatcagc atcgtagagt ttgatcmtgg ctcag              45

<210> SEQ ID NO 39
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 39
gcctccctcg cgccatcagc atctcagagt ttgatcmtgg ctcag              45

<210> SEQ ID NO 40
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
```

<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 40
gcctccctcg cgccatcagc atgtcagagt ttgatcmtgg ctcag          45

<210> SEQ ID NO 41
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 41
gcctccctcg cgccatcagc gacgtagagt ttgatcmtgg ctcag          45

<210> SEQ ID NO 42
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 42
gcctccctcg cgccatcagc gactcagagt ttgatcmtgg ctcag          45

<210> SEQ ID NO 43
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 43
gcctccctcg cgccatcagc gagtcagagt ttgatcmtgg ctcag          45

<210> SEQ ID NO 44
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 44
gcctccctcg cgccatcagc gatgtagagt ttgatcmtgg ctcag    45

<210> SEQ ID NO 45
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 45
gcctccctcg cgccatcagc gcagtagagt ttgatcmtgg ctcag    45

<210> SEQ ID NO 46
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 46
gcctccctcg cgccatcagc gcatcagagt ttgatcmtgg ctcag    45

<210> SEQ ID NO 47
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 47
gcctccctcg cgccatcagc gcgtcagagt ttgatcmtgg ctcag    45

<210> SEQ ID NO 48
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 48
gcctccctcg cgccatcagc gctgtagagt ttgatcmtgg ctcag    45

<210> SEQ ID NO 49
<211> LENGTH: 45
<212> TYPE: DNA

<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(45)
<223> OTHER INFORMATION: /note="Description of Artificial Sequence: Synthetic primer"

<400> SEQUENCE: 49
gcctccctcg cgccatcagc gtagtagagt ttgatcmtgg ctcag          45

<210> SEQ ID NO 50
<211> LENGTH: 45
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(45)
<223> OTHER INFORMATION: /note="Description of Artificial Sequence: Synthetic primer"

<400> SEQUENCE: 50
gcctccctcg cgccatcagc gtatcagagt ttgatcmtgg ctcag          45

<210> SEQ ID NO 51
<211> LENGTH: 45
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(45)
<223> OTHER INFORMATION: /note="Description of Artificial Sequence: Synthetic primer"

<400> SEQUENCE: 51
gcctccctcg cgccatcagc gtcgtagagt ttgatcmtgg ctcag          45

<210> SEQ ID NO 52
<211> LENGTH: 45
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(45)
<223> OTHER INFORMATION: /note="Description of Artificial Sequence: Synthetic primer"

<400> SEQUENCE: 52
gcctccctcg cgccatcagc gtctcagagt ttgatcmtgg ctcag          45

<210> SEQ ID NO 53
<211> LENGTH: 45
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(45)

```
<223> OTHER INFORMATION: /note="Description of Artificial Sequence:
      Synthetic primer"

<400> SEQUENCE: 53
gcctccctcg cgccatcagc gtgcaagagt ttgatcmtgg ctcag            45

<210> SEQ ID NO 54
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 54
gcctccctcg cgccatcagc gtgtcagagt ttgatcmtgg ctcag            45

<210> SEQ ID NO 55
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 55
gcctccctcg cgccatcagt acagtagagt ttgatcmtgg ctcag            45

<210> SEQ ID NO 56
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 56
gcctccctcg cgccatcagt acatcagagt ttgatcmtgg ctcag            45

<210> SEQ ID NO 57
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 57
gcctccctcg cgccatcagt acgtcagagt ttgatcmtgg ctcag            45
```

```
<210> SEQ ID NO 58
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 58
gcctccctcg cgccatcagt actgtagagt ttgatcmtgg ctcag            45

<210> SEQ ID NO 59
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 59
gcctccctcg cgccatcagt agagtagagt ttgatcmtgg ctcag            45

<210> SEQ ID NO 60
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 60
gcctccctcg cgccatcagt agatcagagt ttgatcmtgg ctcag            45

<210> SEQ ID NO 61
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 61
gcctccctcg cgccatcagt agcgtagagt ttgatcmtgg ctcag            45

<210> SEQ ID NO 62
<211> LENGTH: 45
<212> TYPE: DNA
<213> ORGANISM: Artificial Sequence
<220> FEATURE:
<223> OTHER INFORMATION: Description of Artifical Sequence: Synthetic
``` primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 62
gcctccctcg cgccatcagt agctcagagt ttgatcmtgg ctcag          45

<210> SEQ ID NO 63
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 63
gcctccctcg cgccatcagt agtgtagagt ttgatcmtgg ctcag          45

<210> SEQ ID NO 64
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 64
gcctccctcg cgccatcagt atagtagagt ttgatcmtgg ctcag          45

<210> SEQ ID NO 65
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 65
gcctccctcg cgccatcagt atatcagagt ttgatcmtgg ctcag          45

<210> SEQ ID NO 66
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

```
<400> SEQUENCE: 66
gcctccctcg cgccatcagt atcgtagagt ttgatcmtgg ctcag          45

<210> SEQ ID NO 67
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 67
gcctccctcg cgccatcagt atctcagagt ttgatcmtgg ctcag          45

<210> SEQ ID NO 68
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 68
gcctccctcg cgccatcagt atgtcagagt ttgatcmtgg ctcag          45

<210> SEQ ID NO 69
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 69
gcctccctcg cgccatcagt cacgtagagt ttgatcmtgg ctcag          45

<210> SEQ ID NO 70
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 70
gcctccctcg cgccatcagt cactcagagt ttgatcmtgg ctcag          45

<210> SEQ ID NO 71
<211> LENGTH: 45
```

```
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 71
gcctccctcg cgccatcagt cagtcagagt ttgatcmtgg ctcag            45

<210> SEQ ID NO 72
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 72
gcctccctcg cgccatcagt catgtagagt ttgatcmtgg ctcag            45

<210> SEQ ID NO 73
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 73
gcctccctcg cgccatcagt cgagtagagt ttgatcmtgg ctcag            45

<210> SEQ ID NO 74
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 74
gcctccctcg cgccatcagt cgatcagagt ttgatcmtgg ctcag            45

<210> SEQ ID NO 75
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
```

<222> LOCATION: (1)..(45)
<223> OTHER INFORMATION: /note="Description of Artificial Sequence: Synthetic primer"

<400> SEQUENCE: 75
gcctccctcg cgccatcagt cgcgtagagt ttgatcmtgg ctcag    45

<210> SEQ ID NO 76
<211> LENGTH: 45
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(45)
<223> OTHER INFORMATION: /note="Description of Artificial Sequence: Synthetic primer"

<400> SEQUENCE: 76
gcctccctcg cgccatcagt cgctcagagt ttgatcmtgg ctcag    45

<210> SEQ ID NO 77
<211> LENGTH: 45
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(45)
<223> OTHER INFORMATION: /note="Description of Artificial Sequence: Synthetic primer"

<400> SEQUENCE: 77
gcctccctcg cgccatcagt cgtgtagagt ttgatcmtgg ctcag    45

<210> SEQ ID NO 78
<211> LENGTH: 45
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(45)
<223> OTHER INFORMATION: /note="Description of Artificial Sequence: Synthetic primer"

<400> SEQUENCE: 78
gcctccctcg cgccatcagt ctagtagagt ttgatcmtgg ctcag    45

<210> SEQ ID NO 79
<211> LENGTH: 45
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(45)
<223> OTHER INFORMATION: /note="Description of Artificial Sequence: Synthetic primer"

<400> SEQUENCE: 79
gcctccctcg cgccatcagt ctatcagagt ttgatcmtgg ctcag    45

```
<210> SEQ ID NO 80
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 80
gcctccctcg cgccatcagt ctcgtagagt ttgatcmtgg ctcag            45

<210> SEQ ID NO 81
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 81
gcctccctcg cgccatcagt ctctcagagt ttgatcmtgg ctcag            45

<210> SEQ ID NO 82
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 82
gcctccctcg cgccatcagt ctgtcagagt ttgatcmtgg ctcag            45

<210> SEQ ID NO 83
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 83
gcctccctcg cgccatcaga gacagagagt ttgatcmtgg ctcag            45

<210> SEQ ID NO 84
<211> LENGTH: 45
<212> TYPE: DNA
<213> ORGANISM: Artificial Sequence
<220> FEATURE:
```

<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 84
gcctccctcg cgccatcaga gagagagagt ttgatcmtgg ctcag                45

<210> SEQ ID NO 85
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 85
gcctccctcg cgccatcaga gatagagagt ttgatcmtgg ctcag                45

<210> SEQ ID NO 86
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 86
gcctccctcg cgccatcaga gcgagagagt ttgatcmtgg ctcag                45

<210> SEQ ID NO 87
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 87
gcctccctcg cgccatcaga gctagagagt ttgatcmtgg ctcag                45

<210> SEQ ID NO 88
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

```
<400> SEQUENCE: 88
gcctccctcg cgccatcaga gtcagagagt ttgatcmtgg ctcag          45

<210> SEQ ID NO 89
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 89
gcctccctcg cgccatcaga gtgagagagt ttgatcmtgg ctcag          45

<210> SEQ ID NO 90
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 90
gcctccctcg cgccatcaga tacagagagt ttgatcmtgg ctcag          45

<210> SEQ ID NO 91
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 91
gcctccctcg cgccatcaga tagagagagt ttgatcmtgg ctcag          45

<210> SEQ ID NO 92
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 92
gcctccctcg cgccatcaga tatagagagt ttgatcmtgg ctcag          45

<210> SEQ ID NO 93
```

```
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 93
gcctccctcg cgccatcaga tcgagagagt ttgatcmtgg ctcag              45

<210> SEQ ID NO 94
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 94
gcctccctcg cgccatcaga tctagagagt ttgatcmtgg ctcag              45

<210> SEQ ID NO 95
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 95
gcctccctcg cgccatcaga tgcagagagt ttgatcmtgg ctcag              45

<210> SEQ ID NO 96
<211> LENGTH: 45
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(45)
<223> OTHER INFORMATION: /note="Description of Artificial Sequence:
      Synthetic primer"

<400> SEQUENCE: 96
gcctccctcg cgccatcaga tgtagagagt ttgatcmtgg ctcag              45

<210> SEQ ID NO 97
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
```

<221> NAME/KEY: source
<222> LOCATION: (1)..(43)
<223> OTHER INFORMATION: /note="Description of Artificial Sequence:
      Synthetic primer"

<400> SEQUENCE: 97
gccttgccag cccgctcaga gacgtgctgc ctcccgtagg agt         43

<210> SEQ ID NO 98
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 98
gccttgccag cccgctcaga gactcgctgc ctcccgtagg agt         43

<210> SEQ ID NO 99
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 99
gccttgccag cccgctcaga gagtcgctgc ctcccgtagg agt         43

<210> SEQ ID NO 100
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 100
gccttgccag cccgctcaga gatgtgctgc ctcccgtagg agt         43

<210> SEQ ID NO 101
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 101
gccttgccag cccgctcaga gcagtgctgc ctcccgtagg agt         43

<210> SEQ ID NO 102
<211> LENGTH: 43
<212> TYPE: DNA
<213> ORGANISM: Artificial Sequence
<220> FEATURE:
<223> OTHER INFORMATION: Description of Artifical Sequence: Synthetic
    primer
<220> FEATURE:
<221> NAME/KEY: source
<222> LOCATION: (1)..(43)
<223> OTHER INFORMATION: /note="Description of Artificial Sequence:
    Synthetic primer"

<400> SEQUENCE: 102
gccttgccag cccgctcaga gcatcgctgc ctcccgtagg agt         43

<210> SEQ ID NO 103
<211> LENGTH: 43
<212> TYPE: DNA
<213> ORGANISM: Artificial Sequence
<220> FEATURE:
<223> OTHER INFORMATION: Description of Artifical Sequence: Synthetic
    primer
<220> FEATURE:
<221> NAME/KEY: source
<222> LOCATION: (1)..(43)
<223> OTHER INFORMATION: /note="Description of Artificial Sequence:
    Synthetic primer"

<400> SEQUENCE: 103
gccttgccag cccgctcaga gcgtcgctgc ctcccgtagg agt         43

<210> SEQ ID NO 104
<211> LENGTH: 43
<212> TYPE: DNA
<213> ORGANISM: Artificial Sequence
<220> FEATURE:
<223> OTHER INFORMATION: Description of Artifical Sequence: Synthetic
    primer
<220> FEATURE:
<221> NAME/KEY: source
<222> LOCATION: (1)..(43)
<223> OTHER INFORMATION: /note="Description of Artificial Sequence:
    Synthetic primer"

<400> SEQUENCE: 104
gccttgccag cccgctcaga gctgtgctgc ctcccgtagg agt         43

<210> SEQ ID NO 105
<211> LENGTH: 43
<212> TYPE: DNA
<213> ORGANISM: Artificial Sequence
<220> FEATURE:
<223> OTHER INFORMATION: Description of Artifical Sequence: Synthetic
    primer
<220> FEATURE:
<221> NAME/KEY: source
<222> LOCATION: (1)..(43)
<223> OTHER INFORMATION: /note="Description of Artificial Sequence:
    Synthetic primer"

<400> SEQUENCE: 105
gccttgccag cccgctcaga gtagtgctgc ctcccgtagg agt         43

<210> SEQ ID NO 106
<211> LENGTH: 43
<212> TYPE: DNA
<213> ORGANISM: Artificial Sequence

```
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 106
gccttgccag cccgctcaga gtatcgctgc ctcccgtagg agt              43

<210> SEQ ID NO 107
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 107
gccttgccag cccgctcaga gtcgtgctgc ctcccgtagg agt              43

<210> SEQ ID NO 108
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 108
gccttgccag cccgctcaga gtctcgctgc ctcccgtagg agt              43

<210> SEQ ID NO 109
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 109
gccttgccag cccgctcaga gtgtcgctgc ctcccgtagg agt              43

<210> SEQ ID NO 110
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
```

Synthetic primer"

<400> SEQUENCE: 110
gccttgccag cccgctcaga tacgtgctgc ctcccgtagg agt          43

<210> SEQ ID NO 111
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 111
gccttgccag cccgctcaga tactcgctgc ctcccgtagg agt          43

<210> SEQ ID NO 112
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 112
gccttgccag cccgctcaga tagtcgctgc ctcccgtagg agt          43

<210> SEQ ID NO 113
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 113
gccttgccag cccgctcaga tatgtgctgc ctcccgtagg agt          43

<210> SEQ ID NO 114
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 114
gccttgccag cccgctcaga tcagtgctgc ctcccgtagg agt          43

-continued

```
<210> SEQ ID NO 115
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 115
gccttgccag cccgctcaga tcatcgctgc ctcccgtagg agt            43

<210> SEQ ID NO 116
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 116
gccttgccag cccgctcaga tcgtcgctgc ctcccgtagg agt            43

<210> SEQ ID NO 117
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 117
gccttgccag cccgctcaga tctgtgctgc ctcccgtagg agt            43

<210> SEQ ID NO 118
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 118
gccttgccag cccgctcaga tgagtgctgc ctcccgtagg agt            43

<210> SEQ ID NO 119
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
```

```
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 119
gccttgccag cccgctcaga tgatcgctgc ctcccgtagg agt          43

<210> SEQ ID NO 120
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 120
gccttgccag cccgctcaga tgcgtgctgc ctcccgtagg agt          43

<210> SEQ ID NO 121
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 121
gccttgccag cccgctcaga tgctcgctgc ctcccgtagg agt          43

<210> SEQ ID NO 122
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 122
gccttgccag cccgctcaga tgtgtgctgc ctcccgtagg agt          43

<210> SEQ ID NO 123
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 123
```
gccttgccag cccgctcagc acagtgctgc ctcccgtagg agt                            43

<210> SEQ ID NO 124
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 124
gccttgccag cccgctcagc acatcgctgc ctcccgtagg agt                            43

<210> SEQ ID NO 125
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 125
gccttgccag cccgctcagc acgtcgctgc ctcccgtagg agt                            43

<210> SEQ ID NO 126
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 126
gccttgccag cccgctcagc actgtgctgc ctcccgtagg agt                            43

<210> SEQ ID NO 127
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 127
gccttgccag cccgctcagc agagtgctgc ctcccgtagg agt                            43

<210> SEQ ID NO 128
<211> LENGTH: 43
<212> TYPE: DNA

<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(43)
<223> OTHER INFORMATION: /note="Description of Artificial Sequence: Synthetic primer"

<400> SEQUENCE: 128
gccttgccag cccgctcagc agatcgctgc ctcccgtagg agt        43

<210> SEQ ID NO 129
<211> LENGTH: 43
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(43)
<223> OTHER INFORMATION: /note="Description of Artificial Sequence: Synthetic primer"

<400> SEQUENCE: 129
gccttgccag cccgctcagc agcgtgctgc ctcccgtagg agt        43

<210> SEQ ID NO 130
<211> LENGTH: 43
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(43)
<223> OTHER INFORMATION: /note="Description of Artificial Sequence: Synthetic primer"

<400> SEQUENCE: 130
gccttgccag cccgctcagc agctcgctgc ctcccgtagg agt        43

<210> SEQ ID NO 131
<211> LENGTH: 43
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(43)
<223> OTHER INFORMATION: /note="Description of Artificial Sequence: Synthetic primer"

<400> SEQUENCE: 131
gccttgccag cccgctcagc agtgtgctgc ctcccgtagg agt        43

<210> SEQ ID NO 132
<211> LENGTH: 43
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(43)

<223> OTHER INFORMATION: /note="Description of Artificial Sequence:
Synthetic primer"

<400> SEQUENCE: 132
gccttgccag cccgctcagc atagtgctgc ctcccgtagg agt                43

<210> SEQ ID NO 133
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 133
gccttgccag cccgctcagc atatcgctgc ctcccgtagg agt                43

<210> SEQ ID NO 134
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 134
gccttgccag cccgctcagc atcgtgctgc ctcccgtagg agt                43

<210> SEQ ID NO 135
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 135
gccttgccag cccgctcagc atctcgctgc ctcccgtagg agt                43

<210> SEQ ID NO 136
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 136
gccttgccag cccgctcagc atgtcgctgc ctcccgtagg agt                43

```
<210> SEQ ID NO 137
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 137
gccttgccag cccgctcagc gacgtgctgc ctcccgtagg agt                    43

<210> SEQ ID NO 138
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 138
gccttgccag cccgctcagc gactcgctgc ctcccgtagg agt                    43

<210> SEQ ID NO 139
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 139
gccttgccag cccgctcagc gagtcgctgc ctcccgtagg agt                    43

<210> SEQ ID NO 140
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 140
gccttgccag cccgctcagc gatgtgctgc ctcccgtagg agt                    43

<210> SEQ ID NO 141
<211> LENGTH: 43
<212> TYPE: DNA
<213> ORGANISM: Artificial Sequence
<220> FEATURE:
<223> OTHER INFORMATION: Description of Artifical Sequence: Synthetic
``` primer
<220> FEATURE:
<221> NAME/KEY: source
<222> LOCATION: (1)..(43)
<223> OTHER INFORMATION: /note="Description of Artificial Sequence: Synthetic primer"

<400> SEQUENCE: 141
gccttgccag cccgctcagc gcagtgctgc ctcccgtagg agt             43

<210> SEQ ID NO 142
<211> LENGTH: 43
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(43)
<223> OTHER INFORMATION: /note="Description of Artificial Sequence: Synthetic primer"

<400> SEQUENCE: 142
gccttgccag cccgctcagc gcatcgctgc ctcccgtagg agt             43

<210> SEQ ID NO 143
<211> LENGTH: 43
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(43)
<223> OTHER INFORMATION: /note="Description of Artificial Sequence: Synthetic primer"

<400> SEQUENCE: 143
gccttgccag cccgctcagc gcgtcgctgc ctcccgtagg agt             43

<210> SEQ ID NO 144
<211> LENGTH: 43
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(43)
<223> OTHER INFORMATION: /note="Description of Artificial Sequence: Synthetic primer"

<400> SEQUENCE: 144
gccttgccag cccgctcagc gctgtgctgc ctcccgtagg agt             43

<210> SEQ ID NO 145
<211> LENGTH: 43
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(43)
<223> OTHER INFORMATION: /note="Description of Artificial Sequence: Synthetic primer"

<400> SEQUENCE: 145
gccttgccag cccgctcagc gtagtgctgc ctcccgtagg agt            43

<210> SEQ ID NO 146
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 146
gccttgccag cccgctcagc gtatcgctgc ctcccgtagg agt            43

<210> SEQ ID NO 147
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 147
gccttgccag cccgctcagc gtcgtgctgc ctcccgtagg agt            43

<210> SEQ ID NO 148
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 148
gccttgccag cccgctcagc gtctcgctgc ctcccgtagg agt            43

<210> SEQ ID NO 149
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 149
gccttgccag cccgctcagc gtgcagctgc ctcccgtagg agt            43

<210> SEQ ID NO 150
<211> LENGTH: 43

<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(43)
<223> OTHER INFORMATION: /note="Description of Artificial Sequence: Synthetic primer"

<400> SEQUENCE: 150
gccttgccag cccgctcagc gtgtcgctgc ctcccgtagg agt         43

<210> SEQ ID NO 151
<211> LENGTH: 43
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(43)
<223> OTHER INFORMATION: /note="Description of Artificial Sequence: Synthetic primer"

<400> SEQUENCE: 151
gccttgccag cccgctcagt acagtgctgc ctcccgtagg agt         43

<210> SEQ ID NO 152
<211> LENGTH: 43
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(43)
<223> OTHER INFORMATION: /note="Description of Artificial Sequence: Synthetic primer"

<400> SEQUENCE: 152
gccttgccag cccgctcagt acatcgctgc ctcccgtagg agt         43

<210> SEQ ID NO 153
<211> LENGTH: 43
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(43)
<223> OTHER INFORMATION: /note="Description of Artificial Sequence: Synthetic primer"

<400> SEQUENCE: 153
gccttgccag cccgctcagt acgtcgctgc ctcccgtagg agt         43

<210> SEQ ID NO 154
<211> LENGTH: 43
<212> TYPE: DNA
<213> ORGANISM: Artificial Sequence
<220> FEATURE:
<223> OTHER INFORMATION: Description of Artifical Sequence: Synthetic primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 154
gccttgccag cccgctcagt actgtgctgc ctcccgtagg agt                           43

<210> SEQ ID NO 155
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 155
gccttgccag cccgctcagt agagtgctgc ctcccgtagg agt                           43

<210> SEQ ID NO 156
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 156
gccttgccag cccgctcagt agatcgctgc ctcccgtagg agt                           43

<210> SEQ ID NO 157
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 157
gccttgccag cccgctcagt agcgtgctgc ctcccgtagg agt                           43

<210> SEQ ID NO 158
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 158
gccttgccag cccgctcagt agctcgctgc ctcccgtagg agt                           43

```
<210> SEQ ID NO 159
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 159
gccttgccag cccgctcagt agtgtgctgc ctcccgtagg agt                    43

<210> SEQ ID NO 160
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 160
gccttgccag cccgctcagt atagtgctgc ctcccgtagg agt                    43

<210> SEQ ID NO 161
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 161
gccttgccag cccgctcagt atatcgctgc ctcccgtagg agt                    43

<210> SEQ ID NO 162
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 162
gccttgccag cccgctcagt atcgtgctgc ctcccgtagg agt                    43

<210> SEQ ID NO 163
<211> LENGTH: 43
<212> TYPE: DNA
<213> ORGANISM: Artificial Sequence
<220> FEATURE:
```

```
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 163
gccttgccag cccgctcagt atctcgctgc ctcccgtagg agt            43

<210> SEQ ID NO 164
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 164
gccttgccag cccgctcagt atgtcgctgc ctcccgtagg agt            43

<210> SEQ ID NO 165
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 165
gccttgccag cccgctcagt cacgtgctgc ctcccgtagg agt            43

<210> SEQ ID NO 166
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 166
gccttgccag cccgctcagt cactcgctgc ctcccgtagg agt            43

<210> SEQ ID NO 167
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"
```

-continued

<400> SEQUENCE: 167
gccttgccag cccgctcagt cagtcgctgc ctcccgtagg agt                43

<210> SEQ ID NO 168
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE
<221> NAME/KEY: source
<222> LOCATION: (1)..(43)
<223> OTHER INFORMATION: /note="Description of Artificial Sequence:
      Synthetic primer"

<400> SEQUENCE: 168
gccttgccag cccgctcagt catgtgctgc ctcccgtagg agt                43

<210> SEQ ID NO 169
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 169
gccttgccag cccgctcagt cgagtgctgc ctcccgtagg agt                43

<210> SEQ ID NO 170
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 170
gccttgccag cccgctcagt cgatcgctgc ctcccgtagg agt                43

<210> SEQ ID NO 171
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 171
gccttgccag cccgctcagt cgcgtgctgc ctcccgtagg agt                43

<210> SEQ ID NO 172

```
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 172
gccttgccag cccgctcagt cgctcgctgc ctcccgtagg agt          43

<210> SEQ ID NO 173
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 173
gccttgccag cccgctcagt cgtgtgctgc ctcccgtagg agt          43

<210> SEQ ID NO 174
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 174
gccttgccag cccgctcagt ctagtgctgc ctcccgtagg agt          43

<210> SEQ ID NO 175
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 175
gccttgccag cccgctcagt ctatcgctgc ctcccgtagg agt          43

<210> SEQ ID NO 176
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
```

<221> NAME/KEY: source
<222> LOCATION: (1)..(43)
<223> OTHER INFORMATION: /note="Description of Artificial Sequence:
      Synthetic primer"

<400> SEQUENCE: 176
gccttgccag cccgctcagt ctcgtgctgc ctcccgtagg agt                43

<210> SEQ ID NO 177
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 177
gccttgccag cccgctcagt ctctcgctgc ctcccgtagg agt                43

<210> SEQ ID NO 178
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 178
gccttgccag cccgctcagt ctgtcgctgc ctcccgtagg agt                43

<210> SEQ ID NO 179
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 179
gccttgccag cccgctcaga gagcagctgc ctcccgtagg agt                43

<210> SEQ ID NO 180
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 180
gccttgccag cccgctcaga gatcagctgc ctcccgtagg agt                43

<210> SEQ ID NO 181
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 181
gccttgccag cccgctcaga gcacagctgc ctcccgtagg agt                43

<210> SEQ ID NO 182
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 182
gccttgccag cccgctcaga gcgcagctgc ctcccgtagg agt                43

<210> SEQ ID NO 183
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 183
gccttgccag cccgctcaga gctcagctgc ctcccgtagg agt                43

<210> SEQ ID NO 184
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 184
gccttgccag cccgctcaga gtacagctgc ctcccgtagg agt                43

<210> SEQ ID NO 185
<211> LENGTH: 43
<212> TYPE: DNA
<213> ORGANISM: Artificial Sequence

```
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 185
gccttgccag cccgctcaga gtgcagctgc ctcccgtagg agt           43

<210> SEQ ID NO 186
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 186
gccttgccag cccgctcaga tagcagctgc ctcccgtagg agt           43

<210> SEQ ID NO 187
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 187
gccttgccag cccgctcaga tatcagctgc ctcccgtagg agt           43

<210> SEQ ID NO 188
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 188
gccttgccag cccgctcaga tcacagctgc ctcccgtagg agt           43

<210> SEQ ID NO 189
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
```

Synthetic primer"

<400> SEQUENCE: 189
gccttgccag cccgctcaga tcgcagctgc ctcccgtagg agt     43

<210> SEQ ID NO 190
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 190
gccttgccag cccgctcaga tctcagctgc ctcccgtagg agt     43

<210> SEQ ID NO 191
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 191
gccttgccag cccgctcaga tgacagctgc ctcccgtagg agt     43

<210> SEQ ID NO 192
<211> LENGTH: 43
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(43)
<223> OTHER INFORMATION: /note="Description of Artificial Sequence:
      Synthetic primer"

<400> SEQUENCE: 192
gccttgccag cccgctcaga tgtcagctgc ctcccgtagg agt     43

<210> SEQ ID NO 193
<211> LENGTH: 24
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(24)
<223> OTHER INFORMATION: /note="Description of Artificial Sequence:
      Synthetic primer"

<400> SEQUENCE: 193
agctagagtt tgatcmtggc tcag     24

<210> SEQ ID NO 194
<211> LENGTH: 28
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(28)
<223> OTHER INFORMATION: /note="Description of Artificial Sequence:
      Synthetic primer"

<400> SEQUENCE: 194
agctagctag agtttgatcm tggctcag                                          28

<210> SEQ ID NO 195
<211> LENGTH: 28
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(28)
<223> OTHER INFORMATION: /note="Description of Artificial Sequence:
      Synthetic primer"

<400> SEQUENCE: 195
agtcagtcag agtttgatcm tggctcag                                          28

<210> SEQ ID NO 196
<211> LENGTH: 28
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(28)
<223> OTHER INFORMATION: /note="Description of Artificial Sequence:
      Synthetic primer"

<400> SEQUENCE: 196
gatcgatcag agtttgatcm tggctcag                                          28

<210> SEQ ID NO 197
<211> LENGTH: 28
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(28)
<223> OTHER INFORMATION: /note="Description of Artificial Sequence:
      Synthetic primer"

<400> SEQUENCE: 197
gactgactag agtttgatcm tggctcag                                          28

<210> SEQ ID NO 198
<211> LENGTH: 28
<212> TYPE: DNA
<213> ORGANISM: Artificial Sequence
<220> FEATURE:
<223> OTHER INFORMATION: Description of Artifical Sequence: Synthetic
      primer -continued

```
<220> FEATURE:
<221> NAME/KEY: source
<222> LOCATION: (1)..(28)
<223> OTHER INFORMATION: /note="Description of Artificial Sequence:
      Synthetic primer"

<400> SEQUENCE: 198
ctgcctgcag agtttgatcm tggctcag                                             28

<210> SEQ ID NO 199
<211> LENGTH: 28
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(28)
<223> OTHER INFORMATION: /note="Description of Artificial Sequence:
      Synthetic primer"

<400> SEQUENCE: 199
ctagctagag agtttgatcm tggctcag                                             28

<210> SEQ ID NO 200
<211> LENGTH: 28
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(28)
<223> OTHER INFORMATION: /note="Description of Artificial Sequence:
      Synthetic primer"

<400> SEQUENCE: 200
atgcatgcag agtttgatcm tggctcag                                             28

<210> SEQ ID NO 201
<211> LENGTH: 28
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(28)
<223> OTHER INFORMATION: /note="Description of Artificial Sequence:
      Synthetic primer"

<400> SEQUENCE: 201
atagatagag agtttgatcm tggctcag                                             28

<210> SEQ ID NO 202
<211> LENGTH: 28
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(28)
<223> OTHER INFORMATION: /note="Description of Artificial Sequence:
      Synthetic primer"

<400> SEQUENCE: 202
```
atctatctag agtttgatcm tggctcag                                    28

<210> SEQ ID NO 203
<211> LENGTH: 28
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(28)
<223> OTHER INFORMATION: /note="Description of Artificial Sequence:
      Synthetic primer"

<400> SEQUENCE: 203
atatatatag agtttgatcm tggctcag                                    28

<210> SEQ ID NO 204
<211> LENGTH: 22
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(22)
<223> OTHER INFORMATION: /note="Description of Artificial Sequence:
      Synthetic primer"

<400> SEQUENCE: 204
agctgctgcc tcccgtagga gt                                          22

<210> SEQ ID NO 205
<211> LENGTH: 26
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(26)
<223> OTHER INFORMATION: /note="Description of Artificial Sequence:
      Synthetic primer"

<400> SEQUENCE: 205
agctagctgc tgcctcccgt aggagt                                      26

<210> SEQ ID NO 206
<211> LENGTH: 26
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(26)
<223> OTHER INFORMATION: /note="Description of Artificial Sequence:
      Synthetic primer"

<400> SEQUENCE: 206
agtcagtcgc tgcctcccgt aggagt                                      26

<210> SEQ ID NO 207
<211> LENGTH: 26
<212> TYPE: DNA

```
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(26)
<223> OTHER INFORMATION: /note="Description of Artificial Sequence:
      Synthetic primer"

<400> SEQUENCE: 207
gatcgatcgc tgcctcccgt aggagt                                        26

<210> SEQ ID NO 208
<211> LENGTH: 26
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(26)
<223> OTHER INFORMATION: /note="Description of Artificial Sequence:
      Synthetic primer"

<400> SEQUENCE: 208
gactgactgc tgcctcccgt aggagt                                        26

<210> SEQ ID NO 209
<211> LENGTH: 26
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(26)
<223> OTHER INFORMATION: /note="Description of Artificial Sequence:
      Synthetic primer"

<400> SEQUENCE: 209
ctgcctgcgc tgcctcccgt aggagt                                        26

<210> SEQ ID NO 210
<211> LENGTH: 26
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(26)
<223> OTHER INFORMATION: /note="Description of Artificial Sequence:
      Synthetic primer"

<400> SEQUENCE: 210
ctatctatgc tgcctcccgt aggagt                                        26

<210> SEQ ID NO 211
<211> LENGTH: 26
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(26)
```

```
<223> OTHER INFORMATION: /note="Description of Artificial Sequence:
      Synthetic primer"

<400> SEQUENCE: 211
atgcatgcgc tgcctcccgt aggagt                                              26

<210> SEQ ID NO 212
<211> LENGTH: 26
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(26)
<223> OTHER INFORMATION: /note="Description of Artificial Sequence:
      Synthetic primer"

<400> SEQUENCE: 212
atatatatgc tgcctcccgt aggagt                                              26

<210> SEQ ID NO 213
<211> LENGTH: 26
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(26)
<223> OTHER INFORMATION: /note="Description of Artificial Sequence:
      Synthetic primer"

<400> SEQUENCE: 213
atctatctgc tgcctcccgt aggagt                                              26

<210> SEQ ID NO 214
<211> LENGTH: 26
<212> TYPE: DNA
<213> ORGANISM: Artificial Sequence
<220> FEATURE:
<223> OTHER INFORMATION: Description of Artifical Sequence: Synthetic
      primer
<220> FEATURE:
<221> NAME/KEY: source
<222> LOCATION: (1)..(26)
<223> OTHER INFORMATION: /note="Description of Artificial Sequence:
      Synthetic primer"

<400> SEQUENCE: 214
atacatacgc tgcctcccgt aggagt                                              26
```